(12) United States Patent
tran

(10) Patent No.: US 12,216,439 B2
(45) Date of Patent: Feb. 4, 2025

(54) HUB TO SYNC MULTIPLE DEVICES

(71) Applicant: Bao tran, Saratoga, CA (US)

(72) Inventor: Bao tran, Saratoga, CA (US)

( * ) Notice: Subject to any disclaimer, the term of this patent is extended or adjusted under 35 U.S.C. 154(b) by 352 days.

(21) Appl. No.: 17/834,631

(22) Filed: Jun. 7, 2022

(65) Prior Publication Data
US 2023/0393541 A1    Dec. 7, 2023

(51) Int. Cl.
```
G05B 15/02    (2006.01)
G06F 30/27    (2020.01)
G06N 20/00    (2019.01)
G16H 40/20    (2018.01)
G16H 40/67    (2018.01)
```

(52) U.S. Cl.
CPC ............ *G05B 15/02* (2013.01); *G06F 30/27* (2020.01); *G06N 20/00* (2019.01); *G16H 40/20* (2018.01); *G16H 40/67* (2018.01)

(58) Field of Classification Search
CPC ............ H04W 4/00; G06F 1/16; G05B 15/02
See application file for complete search history.

(56) References Cited

U.S. PATENT DOCUMENTS

| | | | |
|---|---|---|---|
| 4,014,321 A | 3/1977 | March | |
| 6,043,492 A | 3/2000 | Lee | |
| 8,000,978 B2 | 8/2011 | Wager | |
| 8,249,731 B2 | 8/2012 | Tran | |
| 8,680,991 B2 | 3/2014 | Tran | |
| 8,747,336 B2 | 6/2014 | Tran | |
| 8,798,607 B1 * | 8/2014 | Kaplan | H04M 1/2757 455/418 |
| 9,445,759 B1 | 9/2016 | Lamego | |
| 9,621,659 B1 * | 4/2017 | Ghazanfari | H04L 67/52 |
| 9,699,859 B1 | 7/2017 | Li | |
| 9,819,754 B2 | 11/2017 | Park | |
| 9,820,658 B2 | 11/2017 | Tran | |
| 10,350,454 B1 | 7/2019 | Li | |
| 10,616,726 B1 * | 4/2020 | Freeman, II | H04W 8/02 |

(Continued)

OTHER PUBLICATIONS

Liu, A Machine Learning Approach to Combining Individual Strength and Team Features for Team Recommendation, Dec. 2014 DOI:10.13140/2.1.4558.4966 2014 IEEE International Conference on Machine Learning and Applications (ICMLA)At: Detroit, Michigan, US.

(Continued)

*Primary Examiner* — Vincent H Tran
(74) *Attorney, Agent, or Firm* — PatentPC Power Patent

(57) ABSTRACT

A method synchronizes a plurality of mobile devices from different vendors by pairing mobile devices with a hub; positioning the hub in an area accessible to group members; automatically copying data structures with characteristics of the mobile device and extracting data from the mobile devices when each of the group members are within a range of the hub; uploading the copied data structures to a remote server; parsing the data based on each respective mobile manufacture data structure; and synchronizing user data with a cloud database. In implementations, the method can be used for fitness training of teams or for selecting optimal team members for a task. The hub's awareness of connected devices in a building can be used to reduce energy consumption by turning off building sectors based on occupants therein.

20 Claims, 15 Drawing Sheets

(56) References Cited

U.S. PATENT DOCUMENTS

| | | | |
|---|---|---|---|
| 11,178,728 B1 | 11/2021 | Gu | |
| 11,189,922 B2 | 11/2021 | Tran | |
| 2002/0069096 A1* | 6/2002 | Lindoerfer | G06Q 10/06375 |
| | | | 705/7.41 |
| 2006/0259586 A1* | 11/2006 | Wood | G06F 16/954 |
| | | | 709/219 |
| 2009/0005116 A1* | 1/2009 | Sharma | H04W 99/00 |
| | | | 455/557 |
| 2010/0168537 A1 | 7/2010 | Ueda | |
| 2010/0280838 A1 | 11/2010 | Bosworth | |
| 2012/0324047 A1* | 12/2012 | Diner | H04W 4/21 |
| | | | 709/217 |
| 2013/0178335 A1 | 7/2013 | Lin | |
| 2014/0086431 A1* | 3/2014 | Martin | H05K 5/03 |
| | | | 381/80 |
| 2015/0227556 A1* | 8/2015 | Kimura | G06F 16/178 |
| | | | 707/620 |
| 2016/0051191 A1* | 2/2016 | Miller | A61B 5/681 |
| | | | 600/300 |
| 2016/0058133 A1 | 3/2016 | Fournier | |
| 2016/0173608 A1* | 6/2016 | Laflen | H04B 7/26 |
| | | | 702/188 |
| 2016/0266606 A1* | 9/2016 | Ricci | G06F 1/163 |
| 2017/0060911 A1* | 3/2017 | Loscalzo | G06F 16/258 |
| 2017/0344726 A1 | 11/2017 | Duffy | |
| 2018/0032605 A1* | 2/2018 | Deshpande | G06F 16/3332 |
| 2018/0035930 A1 | 2/2018 | Sokolov | |
| 2018/0074069 A1 | 4/2018 | Sokolov | |
| 2018/0103111 A1* | 4/2018 | Narayanam | H04L 51/04 |
| 2018/0189073 A1* | 7/2018 | Larabie-Belanger | G06F 8/38 |
| 2018/0247273 A1* | 8/2018 | Tamma | G06Q 10/1095 |
| 2018/0320916 A1* | 11/2018 | Vincitore | G05D 23/1931 |
| 2019/0082286 A1* | 3/2019 | Tata | H04L 43/08 |
| 2019/0180855 A1 | 6/2019 | Sysko | |
| 2019/0244540 A1 | 8/2019 | Errante | |
| 2019/0281370 A1* | 9/2019 | Struhsaker | H04W 4/80 |
| 2020/0152328 A1* | 5/2020 | Bender | G06N 20/00 |
| 2020/0275394 A1* | 8/2020 | Lam | H04W 76/40 |
| 2020/0281482 A1 | 9/2020 | Watkins | |
| 2020/0314926 A1* | 10/2020 | Chen | H04W 76/14 |
| 2020/0406119 A1* | 12/2020 | Woltermann | H04N 21/44 |
| 2021/0086030 A1* | 3/2021 | Kashyap | G06N 20/00 |
| 2021/0150380 A1* | 5/2021 | Verteletskyi | G06F 16/906 |
| 2021/0178226 A1* | 6/2021 | Abecassis | G06F 16/215 |
| 2021/0225483 A1* | 7/2021 | Likovich | G16H 50/20 |
| 2021/0333769 A1* | 10/2021 | Shah | G06Q 20/3415 |
| 2022/0104151 A1* | 3/2022 | Ly-Gagnon | H04W 76/15 |
| 2022/0108781 A1* | 4/2022 | Hendricks | G01C 21/3635 |
| 2022/0133194 A1* | 5/2022 | Bach | A61B 5/6801 |
| | | | 600/544 |
| 2022/0240347 A1* | 7/2022 | Lee | H04L 51/046 |
| 2022/0311528 A1* | 9/2022 | Jain | H04H 60/70 |
| 2022/0385063 A1* | 12/2022 | Protzman | H05B 47/105 |
| 2023/0272934 A1* | 8/2023 | Mohos | F24D 19/1009 |
| | | | 700/276 |
| 2024/0107503 A1* | 3/2024 | Lee | G06F 3/165 |

OTHER PUBLICATIONS

Polar Inc., Polar Measurement Data Specification for 3rd Party, available at https://github.com/polarofficial/polar-ble-sdk.

* cited by examiner

FIG. 12C

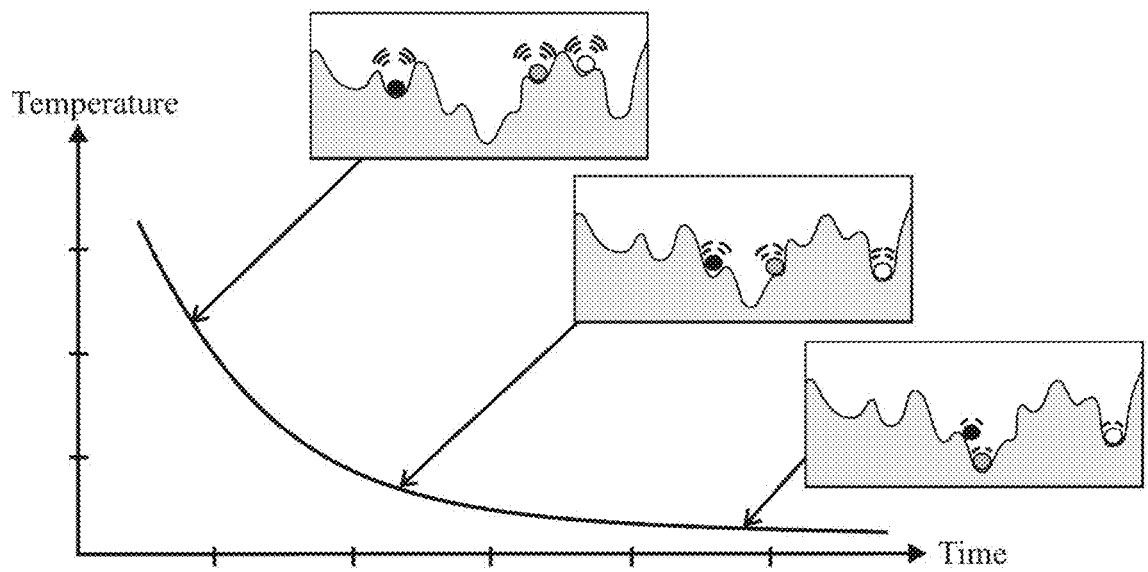

FIG. 3

| |
|---|
| Pairing mobile devices with a hub; |
| Positioning the hub in an area accessible to group members; |
| Automatically copying data structures with characteristics of the mobile device and extracting data from the mobile devices when each of the group members are within a range of the hub; |
| Uploading the copied data structures to a remote server; |
| Parsing the data based on each respective mobile manufacture data structure; and |
| Synchronizing user data with a cloud database. |

FIG. 7

| |
|---|
| Team leaders/coaches create plans that lay out a sequence of programs for all the relevant groups they want to train. |
| Members are assigned to one or more groups |
| Members register their mobile devices with the hub |
| Members enter a gym or a selected location containing the hub |
| Hub automatically collects personal data from the mobile exercise devices from various manufacturers and uploads to a cloud server |
| Cloud server updates data for each user including KPI and KPV, health parameters, weight, height, among others. |
| Apply team training protocols to each member. |
| Team leaders/coaches review each member's progress on the plans and update the sequence of programs for all the relevant groups. |

FIG. 8

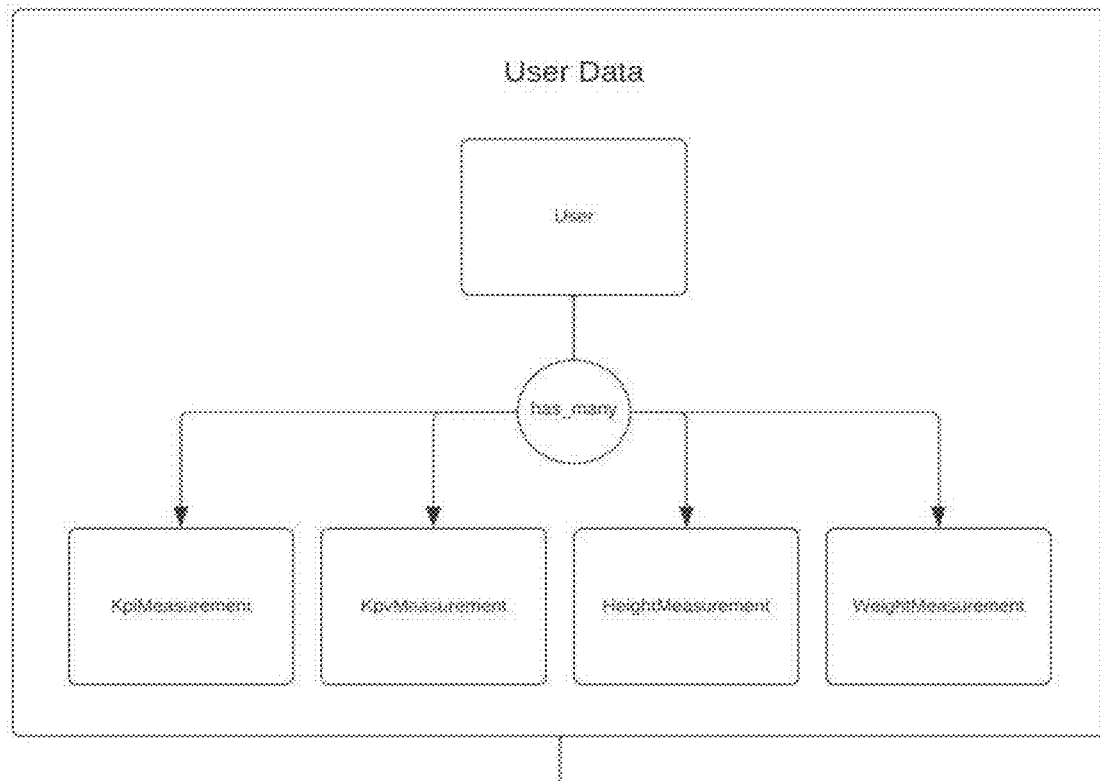

FIG. 13

| |
|---|
| Team leaders/coaches create plans that lay out a sequence of programs for all the relevant groups they want to train. |
| Members are assigned to one or more groups |
| Members register their mobile devices with the hub |
| Members enter a gym or a selected location containing the hub |
| Hub automatically collects personal data from the mobile exercise devices from various manufacturers and uploads to a cloud server |
| Cloud server updates data for each user including KPI and KPV, health parameters, weight, height, among others. |
| Apply team training protocols to each member. |
| During Training: Team leaders/coaches review each member's progress on the plans and update the sequence of programs for all the relevant groups. |
| Pre-Deployment Team Match: Team leaders/coaches identify common requirements (for example speed, strength, expertise in language/skill,...) to AI system (deep learning/expert system or simulated annealing) and provide exercise/program data, training data, and prior mission data to AI system for training and to create one or more AI models/expert system rules |
| During Deployment: Team leaders/coaches provide current mission's requirements to deep learning/expert system for recommendation. AI system applies AI models/expert system rules to current data and checks the latest temporal data from wearable/mobile fitness data and makes recommendations. Compressed/reduced version of the AI models is provided to field team leaders or tactical commanders for local operation or adaptation or in case access to cloud is unavailable. |

FIG. 15

| |
|---|
| Check occupancy sensing via mobile device activities collected by the hub, and |
| if no one is in a room, turn off one or more appliances such as lighting and display terminals in the room and turn off heat or AC (ventilation system) to save energy and reduce greenhouse gas emission; |
| else |
|   Turn on light and ventilation system based on occupancy to reduce greenhouse gas emission; |
|   Adjust air management system for the number of occupants detected |
|   Check for symptoms of Covid (temperature/heart rate/breathing rate) of occupants in a room |
|     If symptoms detected then |
|       Warn occupants of risk; |
|       Enforce minimum distancing requirements; and |
|       Increase air flow in the room and vent air in room to outside (no recirculation) |

HUB TO SYNC MULTIPLE DEVICES

The present system relates to automatic synchronization of data from a group of devices that do not share data with each other or are otherwise incompatible.

BACKGROUND

This section contains background information that is relevant to the disclosure, but it is not necessarily prior art. Bluetooth has been around a long time in the smart home space and is integrated into hundreds of smart devices. It has some serious advantages because it uses very low energy as a communication protocol which means battery powered Bluetooth devices can last a long time. However, the syncing of data from these devices is difficult. For example, gathering data from wearables to gain insights & to advance the fitness and well-being of users requires the users in the loop to sync the devices. Conventional syncing of data can be done from wearable devices to the cloud via a mobile phone connection or a USB connection. Commercial wearable devices often rely on middleware devices such as phones to sync, and compliance & consistency of upload is a persistent challenge. Further, each wearable company has different techniques to syncing data from device to smartphone or USB port. For example, a watch can transfer data from a watch to its app wirelessly via Bluetooth connection. Alternatively, a user can sync the watch with a web service by using a USB port and PC software. While this is acceptable for single user, this requirement is not workable in a group setting such as an athletic team (football team or soccer team, for example) or a military team (such as a battalion), among others. Similarly, the proliferation of Bluetooth devices in the home means that each device communicates only with its manufacturer's database and thus an integrated view of data from all devices requires accessing multiple cloud databases.

SUMMARY

The present application has several inventive aspects including energy management to reduce greenhouse emission:

Hub Sync

In one aspect, a hub automatically syncs and uploads data from a plurality of mobile devices including personnel data to a performance data management system. The hub replaces a traditional intermediary device (i.e. mobile phone, tablet, etc.) with a hotspot (or designated location/base station). The hub provides users with a proximity-based solution that pulls the associated data within its range allowing for consistent data ingest and reducing human error. The hub eliminates the need for the personal-use device (i.e. mobile phone, tablet, etc.) or manual USB upload for future commercial wearables needed in a training environment.

In another aspect, a method synchronizes a plurality of mobile devices from different vendors by pairing mobile devices with a hub; positioning the hub in an area accessible to group members; automatically copying data structures with characteristics of the mobile device and extracting data from the mobile devices when each of the group members are within a range of the hub; uploading the copied data structures to a remote server; parsing the data based on each respective mobile manufacture data structure; and synchronizing user data with a cloud database. In implementations, the method can be used for fitness training of teams or for selecting optimal team members for a task.

Implementations may include one or more of the following:

"Forced synchronization" of known wearables on users, no user action needed. Data synchronization without need of a personal smartphone & without need of a manual selection or "button press" by a user, with Status of sync is provided with date/time group.

Ability to place hub in tactical locations & linking device/account to hub Hub will identify assigned wearables, connect, pulls data from device and push data to a cloud storage provider (CSP). Data synchronization with at least 40 people at same time, and 2 devices per person.

Wireless connection, such as Bluetooth, that allows hub to capture wearable data, store data in non-volatile memory in case of low connective to CSP, and upload the data to CSP.

Advantages of the above aspect may include one or more of the following. The hub passively collects & uploads wearable data from assigned commercial off-the-shelf wearables on personnel to a human performance data management system. The hub replaces a traditional intermediary device (i.e. mobile phone, tablet, etc.) with the hub including hardware and software integration, communication solution to commercial cloud services with potential to move to military networks. For team tracking, this approach automatically sync's each user data upon being near the hub, eliminating the need to constantly syncing devices to his/her accounts on each device manufacturer database and then to the CSP, and thus the hub enables scalable data fitness collection for a large group.

Energy Saving to Reduce Greenhouse Emissions

In implementations, the hub reduces energy usage by controlling a building management system (BMS) based on a number of mobile devices communicating with the hub and locations of the mobile devices. The hub can get accurate in-door positioning through RF triangulation among multiple PAN devices, or simply by using multiple services (GPS, Glonass, Galileo, and BeiDou, among others). Thus, if the hub detects user presence/activities only in a portion of a building, the hub instructs a building management system to minimize energy usage for lighting/heating in unused sectors of the building. The resulting energy savings mitigate climate change by reducing greenhouse gas emissions.

Health Management and Pandemic Management

In yet other implementations, the hub protects occupants by managing in-door air quality. The hub identifies team members with a pandemic symptom or an endemic symptom by looking up temperature and heart rate of occupants and if the pattern fits Covid pattern, for example, the system then increases air flow or air quality in a building according to a number of mobile devices in a sector (indoor positions) of the building that are communicating with the hub. The hub can also restricts entry to the sector and enforces the minimum separation between occupants (such as the 6 ft separation rule for Covid, for example) by texting the mobile devices and advising occupants of the risks.

High Performance Sports Management

Other aspects of the present system relate to customizable product lines or layers, including (1) strength and conditioning, (2) mental performance training, (3) injury prevention and rehabilitation, (4) nutrition and supplementation, and (5) advanced athlete tracking. This can be done with or without the sync hub detailed above. The automated data collection capability of the present system supports a cadence for the frequency of data capture and evaluation with the decision tree or AI logic. With the present tools, coaches and team leaders can embed testing and data collection right into the training process with minimal interruption to the training program or the coach's workflow. Once the decision tree logic is defined, the data collection process is solid at an appropriate cadence, the data capture capability allows coaches to see if the decisions get carried out. The logic trees deliver the right training to the right athlete at the right time.

In implementations, a web-based spreadsheet is used to allow building training programs in a way that feels natural and intuitive. After building a program once, the user can deploy it to as many athletes as you need and quickly make changes or build variants without modifying the original. Programs can be periodized or dynamic, and the user can program for any modality, not just strength training. A training load visualizer can be used to quickly review the makeup of a planned program or analyze the characteristics of an athlete's past training. This tool gives a snapshot of any training variable over time—reps, weight, distance, watts, calories, time, speed, heart rate—in terms of both volume and intensity to enable easy to use scientifically-backed training and conditioning programs. The coach can plan and organize training for athletes over any period of time (annual plans, quadrennial plans, one month plans, etc.). Users can see the big picture for the entire training cycle in a single view, and easily make changes to the plan as circumstances require. The lead coach can involve every coach on the team to coordinate all training and rehab activities so that athletes receive seamless, holistic care.

Advantages of the strength and conditioning system may include one or more of the following. The software's key benefits may include: Extremely fast program design using spreadsheet-like functionality, collaboration among coaches, scientists, and sports medicine staff to create a cohesive, holistic plan, long-term planning with the ability to quickly adapt for injuries and changing schedules, and seamless execution of both in-person and remote training using the tablet and mobile interfaces.

Instead of spending lots of time writing sets and reps while the world changes and evolves, the system empowers coaches to collaborate and implement a more holistic, high-performance approach. The system has all the instruments coaches need to compose and orchestrate health and performance masterpieces. Provide the most comprehensive care and the best possible programming, no matter the sport team being coached or the number of athletes being supervised.

Altogether, the system provides more individualization and produce better outcomes. Coaches spend less time monkeying around in spreadsheets and more time practicing the art and science of high-performance training. The system supports a high ratio of athletes-to-coaches with attendant benefits in customization, accountability, communication. The system provides Cost & Time Savings and allows strength coaches to go completely paperless while programming training—for teams, groups or individuals. Rapid analytics is done. The platform "crowdsources" performance data from athletes via the smartphone and tablet app, with lots of performance reports. The system provides coaches and athletes with a digital environment that promotes accessibility, accountability & interaction outside the weight room. Coaches can easily create specific developmental programs for each individual athlete. Accountability is increased and coaches can track who is working hard and who isn't, especially when an athlete isn't with the team. Communication is improved even with the high ratio between athlete and coach and reduce injuries to players, misalignment, and difficult exercises. An injured athlete might communicate the injury to the trainer, and the Medical Staff, Training Staff, or Athlete may misunderstand the severity of the injury or the rehabilitation plan. If athletes have difficulty performing difficult exercises they can communicate with the coach and to the Strength and Conditioning coach who can modify a player's training plan to increase size and muscle mass.

AI Based Updating of Training Program and Personnel Recommendations

In an alternative embodiment, deep learning is used to extract important variables and relationships to automatically adjust the training routine on behalf of the coach. In another aspect, a system for suggesting optimum team formation is detailed where the AI/deep learning system can be used to recommend team members based on a project requirement. As decision makers such as team leaders (in military/commercial settings) or strength & conditioning professionals (in sports settings) are often overburdened as it is. They are responsible for the health and performance of many athletes at once, so it's a battle to find time for improving processes and becoming more efficient. It usually happens incrementally over a long time. The system can create automated logic and workflow where collecting data, making decisions, and prescribing training interventions, all part of a seamless, automated process.

In a military embodiment, the system provides a method of improving a skill set of an soldier, comprising the steps of determining a skill profile of each of a set of soldiers; determining a set of characteristics of required for a project, the characteristics and the skill profile having correlated features; selecting an available soldier having a skill profile anticipated to be sufficient to handle the project, said skill profile being indicative of a lower level of skill with respect to at least one of the set of characteristics than another available soldier; and adding the selected available soldier to the team and employing the project as a training exercise. Advantageously, the selected soldier may not be penalized based on performance during the training exercise. The skill profile may be updated after the training exercise to represent a higher level of skill with respect to the characteristics of the project, and/or based on a utility of the project. The selecting may be based on an optimization of the utility and cost of the communication, the soldier training resulting from the training exercise being a component of the utility. The soldier selection may also be optimized based on a cost-utility function, said cost-utility function comprising a valuation of immediate costs and utilities and a valuation of persistent soldier training costs and utilities. The system can also be applied in embodiments with commercial uses as well. For example, assemblers in a factory, or delivery people in a warehouse, or call center agents can be optimized using the present system.

In another aspect, the system can be a team recommendation framework which considers both individual and team level characteristics for team recommendation. A first deep learning machine is applied to learn the weight of each feature from prior project outcomes. A team strength score is generated using the weighted features, and a second deep learning machine is applied to find the approximate optimal team. Then an expert system or ruled based (if then) engine is applied to make the final recommendations. The rules-based assignment engine may perform a thorough, programmatic comparison between project needs and requirements and personnel factors including qualifications, skills, workload, strength, speed, equipment familiarity, social relationship with other team members, availability and other factors. In embodiments, the assignment engine may access documentation or records to identify necessary qualifications or factors which may guide the assignment specific people to the project. According to embodiments of the invention in a further regard, a coach or team manager may manipulate a management application or interface to accept or override given personnel assignments, to evaluate alternate providers, to view resulting matches to project requirements, to adjust various schedules and view other simulations or projected results or schedules. According to embodiments of the invention in a further regard, the management interface may flag potential conflicts between a provider's background and a project's needs. For example a supervisor may be alerted that the reassignment of a person to a project may be contraindicated by skill, certification, strength, scheduling or other factors. In some cases, the engine can recommend a person who is suboptimal with a profile which indicates that the person is likely capable of handling the work, but requires training with respect to calls having the set of identified characteristics.

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention as will be described. Accordingly, other objects and a fuller understanding of the invention may be had by referring to the following Detailed Description of the preferred embodiment.

BRIEF DESCRIPTION OF THE DRAWINGS

FIG. 3 shows an exemplary process for syncing multiple wearable devices through the hub.

FIG. 7 shows an illustrative use of the hub of FIGS. 1-6 in group training.

FIG. 8 shows an exemplary user data diagram.

FIG. 12C shows an exemplary simulated annealing operating to determine optimum team member selection by fitting characteristics of each member to serve the team mission.

FIG. 13 shows an exemplary process for matching team members to a task or project.

FIG. 15 shows an exemplary process to save energy and reduce greenhouse gas emissions.

Similar reference characters refer to similar parts or steps throughout the several views of the drawings.

For a more complete understanding of the present invention and the advantages thereof, reference should be made to the following Detailed Description taken in connection with the accompanying drawings.

DETAILED DESCRIPTION OF THE PREFERRED EMBODIMENTS

Figure 1:
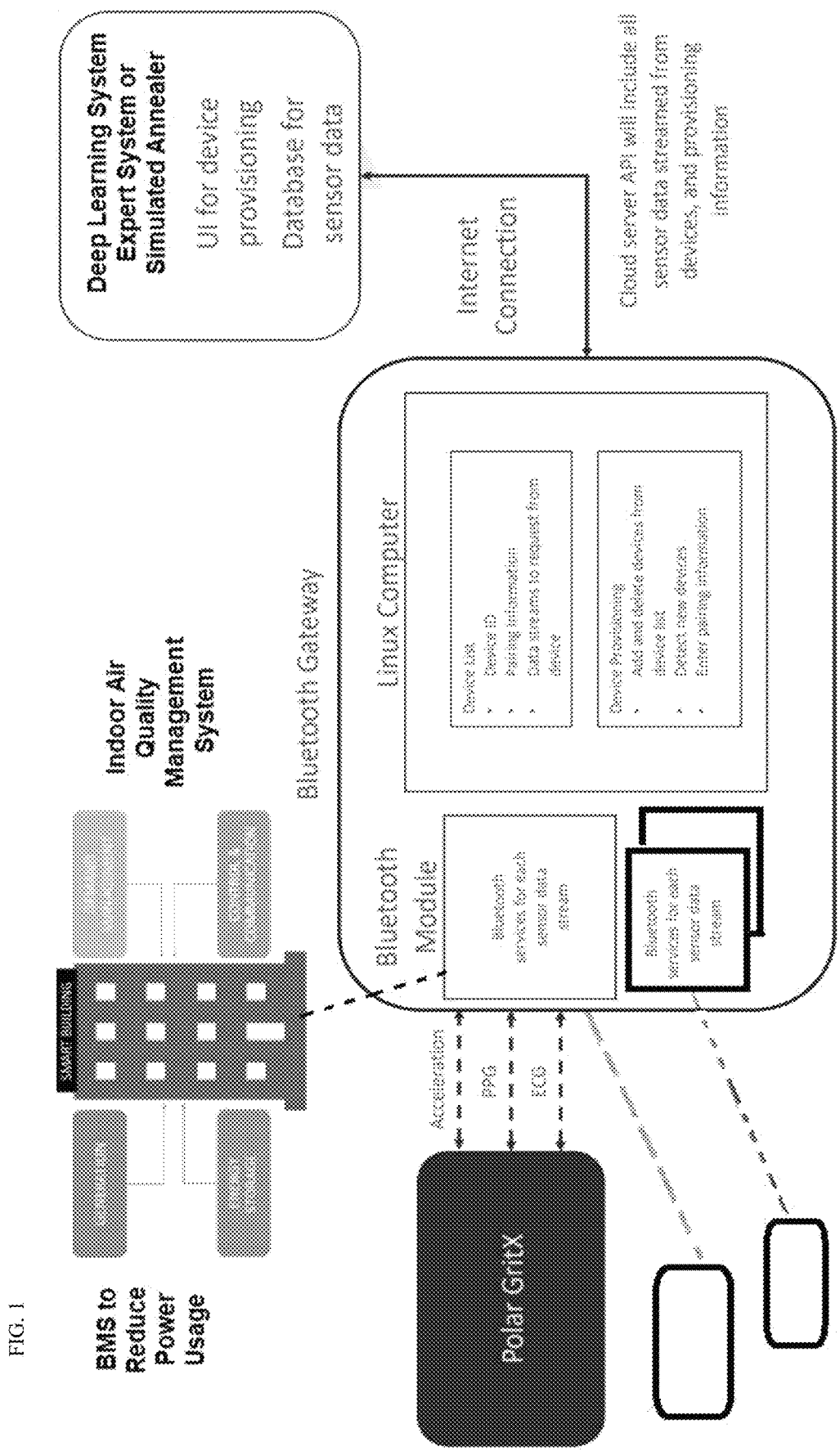
FIG. 1 shows an exemplary architecture of HubSync with a Linux computer in communication with a BMS to manage energy savings and to improve air quality.

FIG. 1 shows an exemplary HubSync system to mitigate climate change by reducing greenhouse gas emissions. The hub can be used to mitigate climate change by reducing greenhouse gas emissions with automated building management. Based on the occupancy as detected by wearable and mobile devices, the hub can reduce energy consumption in unoccupied offices. Moreover, in case of Covid management, the hub can enforce distance separation by only allowing a predetermined number of users to be in an office/enclosed space, and further improve indoor air quality when needed by increasing fan speed if needed.

Figure 14:
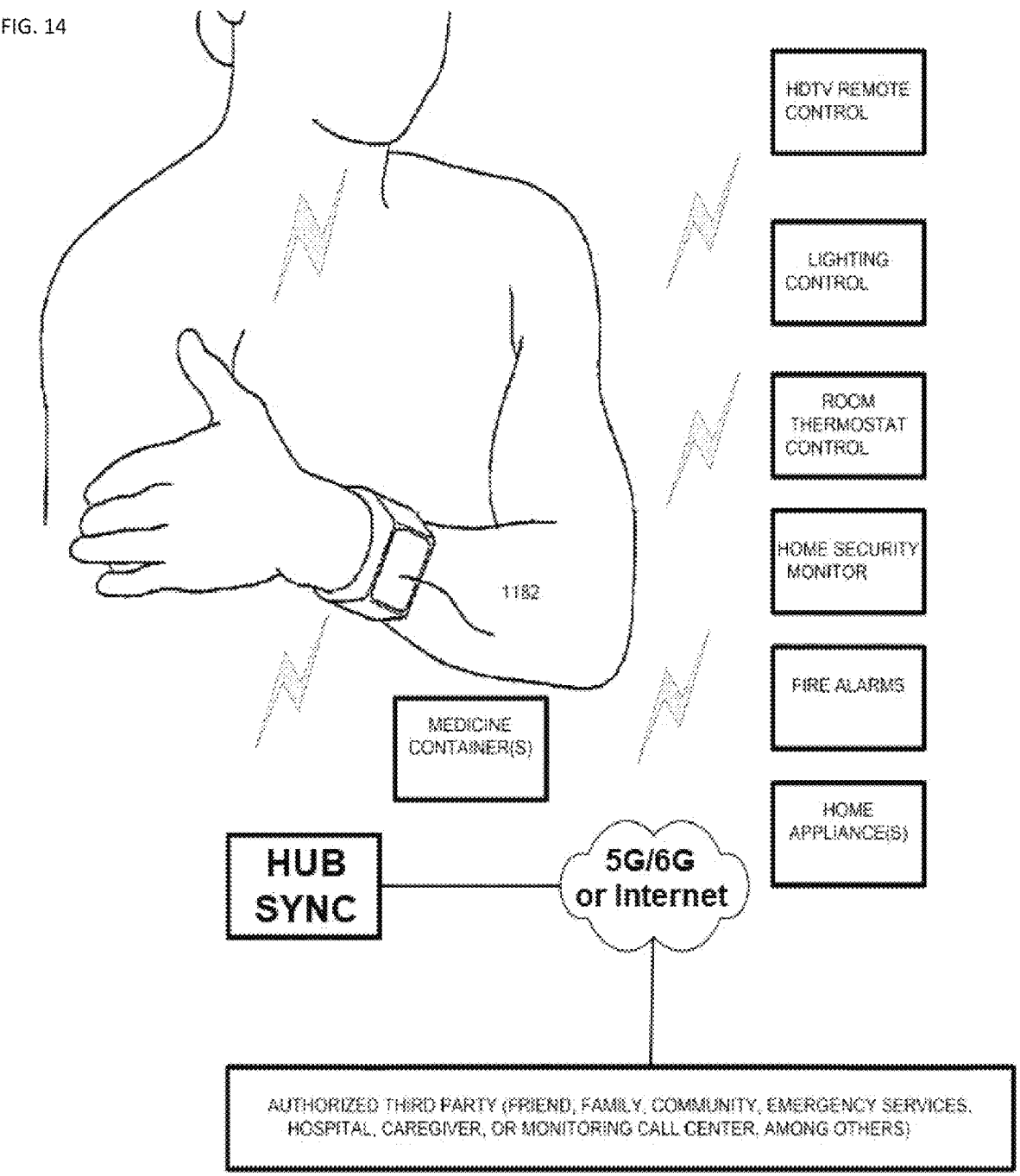
FIG. 14 shows an exemplary home monitoring system where the hub communicates with an array of appliances to protect and serve the user.

In a parallel use, a HomeSync system collects data from a plurality of home automation appliances and makes home safety and convenience decisions for the user, as discussed in more details below with reference to FIG. 14.

Figure 2:
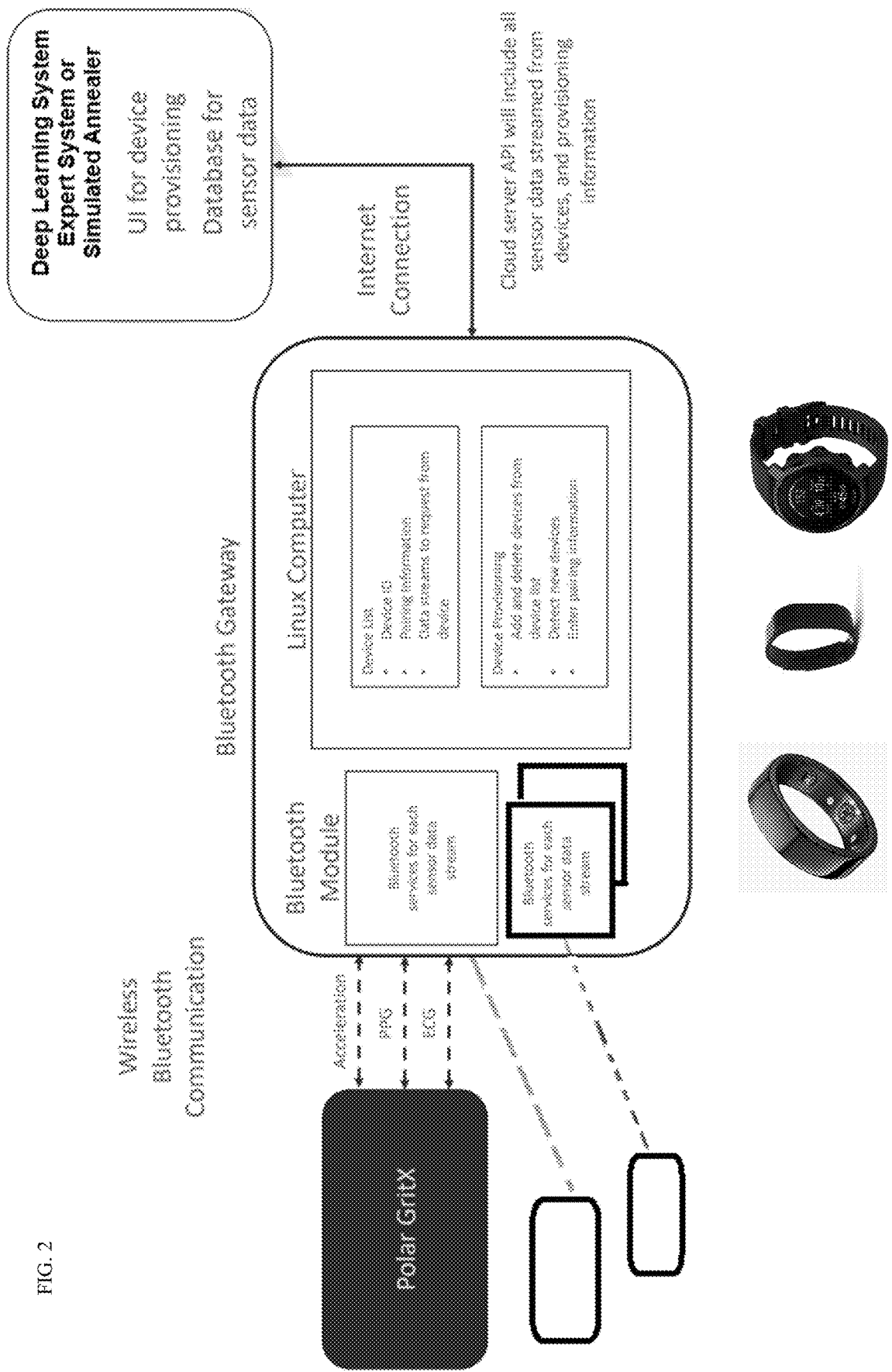
FIG. 2 shows an exemplary GymSync architecture with Linux computer acting as a Bluetooth hub/gateway and a wearable device.

In a further use, FIG. 2 shows an exemplary system called GymSync where data from various wearable devices such as the Oura Ring, Polar GritX and Readiband are captured through one or more Bluetooth (BLE) hubs and data synchronized with a cloud database. A commercial off the shelf (COTS) linux computer acts as a BLE hub/gateway with custom software to enable group synchronization of data as follows:

1. Create Bluetooth services on the hub/gateway to pair with and gather data from the 3 types of wearable devices (Oura Ring, Polar GritX and Readiband)
2. An application will be written on the hub to:
   1) Add and remove devices from the hub
   2) Connect to a specified device and gather data from it
   3) Send all device data to CSP server via CSP API.
   4) The hub will have battery backed data storage device to save data until data synchronization is confirmed.
   5) The hub communicates with the cloud storage API to perform messaging between the hub and the cloud server.

The system performs the following:

Ability to place hub in tactical locations & linking device/account to hub

"Forced synchronization" of known wearables on users, no user action needed. Data synchronization without need of a personal smartphone & without need of a manual selection or "button press" by a user Hub will identify assigned wearables, connect, pulls data from device and push data to a cloud storage provider (CSP).

Status of sync is provided with date/time group

Data synchronization with at least 40 users at same time, and 2 devices per user.

Wireless connection, such as Bluetooth, that allows hub to capture wearable data, store data in non-volatile memory in case of low connective to CSP, and upload the data to CSP Compatibility with a variety of sensors in commercial wearable devices Viewing FIGS. 2-6 together, an exemplary operation of the hub using a Linux embedded computer acting as a Bluetooth hub/gateway with an example wearable device such as the Polar GritX is detailed next. GymSync hub is a device that connects Bluetooth based products to other devices or hardware. Its ROM firmware executes a built-in real-time operating system and handles all interactions with the hardware. At the same time, the ROM firmware includes a full complement of Bluetooth service layers including those supporting the essential Bluetooth Generic Attribute Profile (GATT) and generic access profile (GAP). The hub has battery back-up and is portable for placement in tactical locations. It has wireless connections, such as Bluetooth, that allows hub to capture data from wearables and upload data to CSP cloud storage.

The hub is a long-range Bluetooth gateway/router designed for enterprise deployments. It extends Bluetooth range with open space, line-of-sight, and enables remote control of multiple Bluetooth Low Energy (BLE) devices without requiring any changes to the Bluetooth end devices themselves. The Restful APIs are designed to integrate directly into the application/server using an HTTP/HTTPS based communication protocol, which provides programming language flexibility. The Restful APIs:

a. Connect and control BLE devices.
b. Support three modes: Scanning, Connecting, Broadcasting.
c. Write/read data to/from the BLE device via the Cloud server.
d. Read data as notification/indication events from the BLE device via the Cloud server.
e. Support multiple uplink networking interfaces to flexibly adapt to various environments.

The board provides RESTful APIs for the business to do data collection, positioning, roaming, and security policy management, enabling the remote control of Bluetooth routers across the Internet. The system can operate the BLE devices via the AC's access to the hub using a set of RESTful APIs.

In the Bluetooth protocol, a lookup table called the Generic ATTribute Profile (GATT) database defines the nature and capabilities of a Bluetooth connection through a set of defined services that each comprise a set of supported characteristics. Serving a more fundamental role than GATT services, the Bluetooth generic access profile (GAP) for a device defines how it advertises itself for discovery by the network and how it establishes connections once discovered. The API support the ability to connect/disconnect to a target device. To discover GATT services and characteristics, the board supports the following:

Discover all services and characteristics and all characteristics in one service
Discover all descriptors in one characteristic
Discover a specific service by service/characteristics UUID
Discover all services, characteristics, and descriptors all at once The read/write operations are based on the handle of a specific characteristic. The handle of a specific characteristic can be found in the discovery result. Commands are provided to get advertise data, begin advertise data and stop advertise data.

The software syncs wearable data within a certain range of the hub without need of a personal smartphone and without need of a manual selection or "button press" by a user so this is called "forced synchronization" of known wearables on users. Data synchronization occurs frequently (for example every 15 minutes) and in bulk.

Users need to pair Bluetooth watches to the Bluetooth hub device so that the hub can send data from the Bluetooth device to the cloud. The hub device automatically registers the Bluetooth device by sending the endpoint information of the Bluetooth device to the cloud server. The Bluetooth hub works by scanning for Bluetooth devices. Once it manages to find a device, it caches the data structures of characteristics and services of the device. When the Bluetooth hub processes an HTTP request for the data structure then it uses the cached data for responding to most of these requests. However, if there is a request for real data from the Bluetooth device then the hub will initiate a connection with the Bluetooth device and fetch the data. The software creates Bluetooth services on the hub/hub to pair with and gather data from the 3 types of wearable devices. An application on the hub will:

1. Add and remove devices from the hub
2. Connect to a specified device and gather data from it
3. Send all device data to CSP server via CSP API.

The app provisions all three types of wearable devices (Oura Ring, Polar GritX, and Readiband) and connects to many devices, for example 40 people each wearing two wearable devices, at a time and streams data from each device and sends data received from devices to cloud server. The hub will have battery backed data storage device to save data until data synchronization is confirmed. The hub communicates with the CSP API which defines the messaging between the hub and the server.

In one embodiment the CSP is an edge computing, real time analytics and parsing software that is capable of making decisions at the edge and initiating triggers for other actions or devices. In its simplest form, the CSP acts as an agent to retrieve BLE data from the 3 or more different physical sensor types and pushes the data to the cloud. The CSP will efficiently hold GATT and GAP profiles to ensure seamless communication with the sensors deployed on individuals. As this data is collected, the CSP will place the data into any custom database. This data collection will occur any time a device comes within range of the hub through forced synchronization. The sensor will dump its payload into the hub and then disconnect once the transfer is completed to allow for other incoming BLE connections from other devices and users. The CSP can interface with over 95% of the protocols on the market (if not more), and will readily handle any incoming standard BLE connections, even at high volumes, without an issue. It can even be further expanded to other devices using other protocols with minimal effort if that is ever needed to further expand the devices that the user team or the military units would like to use to track exercise data. The CSP is extremely secure and versatile and will provide this solution with all the functionality required while also having major expansion capabilities in the future as the solution continues to evolve and is deployed in more locations. Also, the edge software can interface with any on-prem/cloud or database required with minimal set up time as the software was built with this intention in mind. As requested by the user, the system can provide real time analytics, edge dashboards per individual user or group of users, and even create trigger events or alerts based on requirements determined by the client.

FIG. 3 shows an exemplary process to collect group performance data from different mobile manufacturers by:
Pairing mobile devices with a hub;
Positioning the hub in an area accessible to group members;
Automatically copying data structures with characteristics of the mobile device and extracting data from the mobile devices when the group members are within a range of the hub;
Uploading the copied data structures to a remote server;

Parsing the data based on each respective mobile manufacture data structure; and Synchronizing user data with a cloud database.

Figure 4:
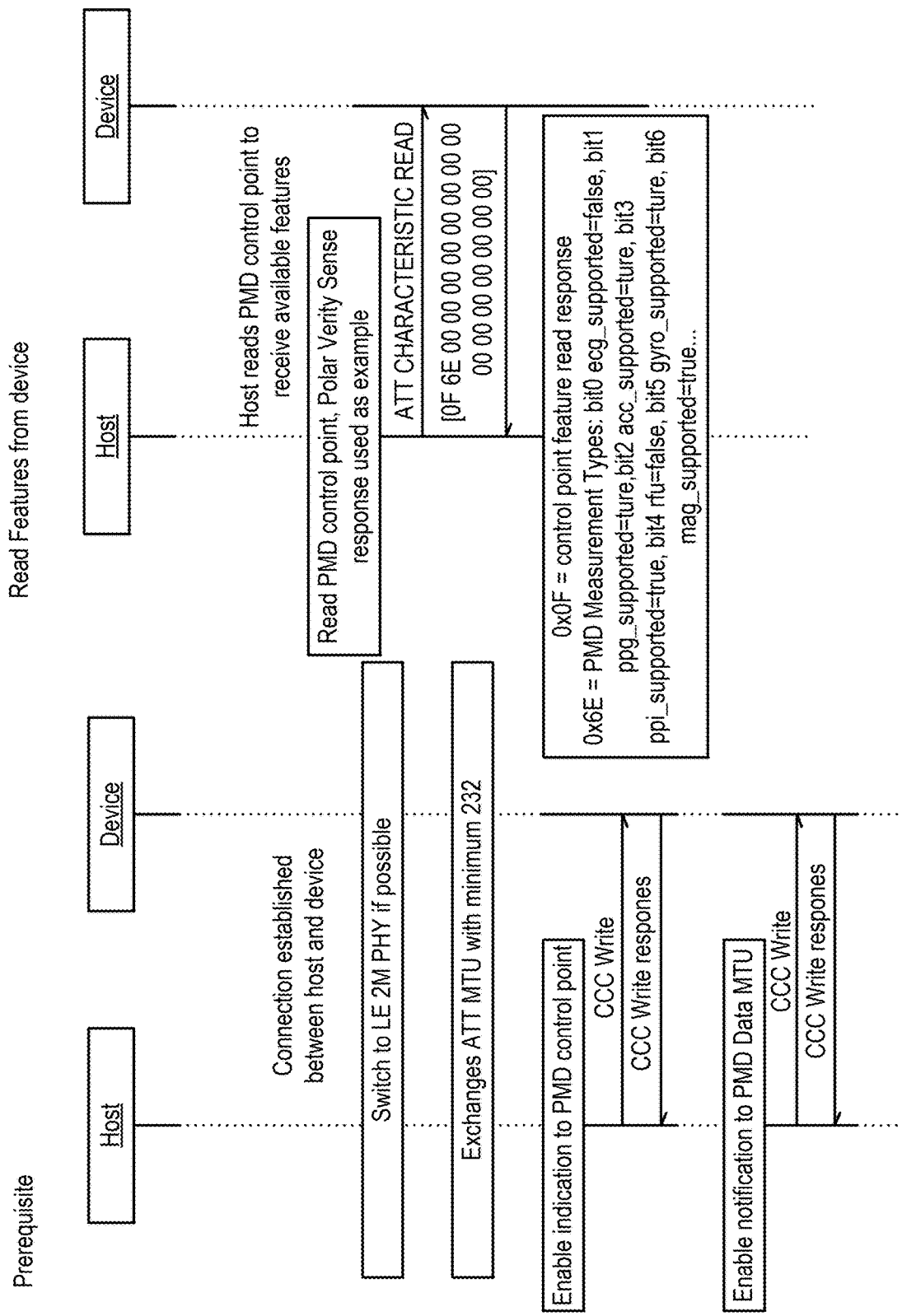
FIGS. 4-5 and 6A-6B show exemplary GATT communications for a selected wearable watch.
Figure 5:
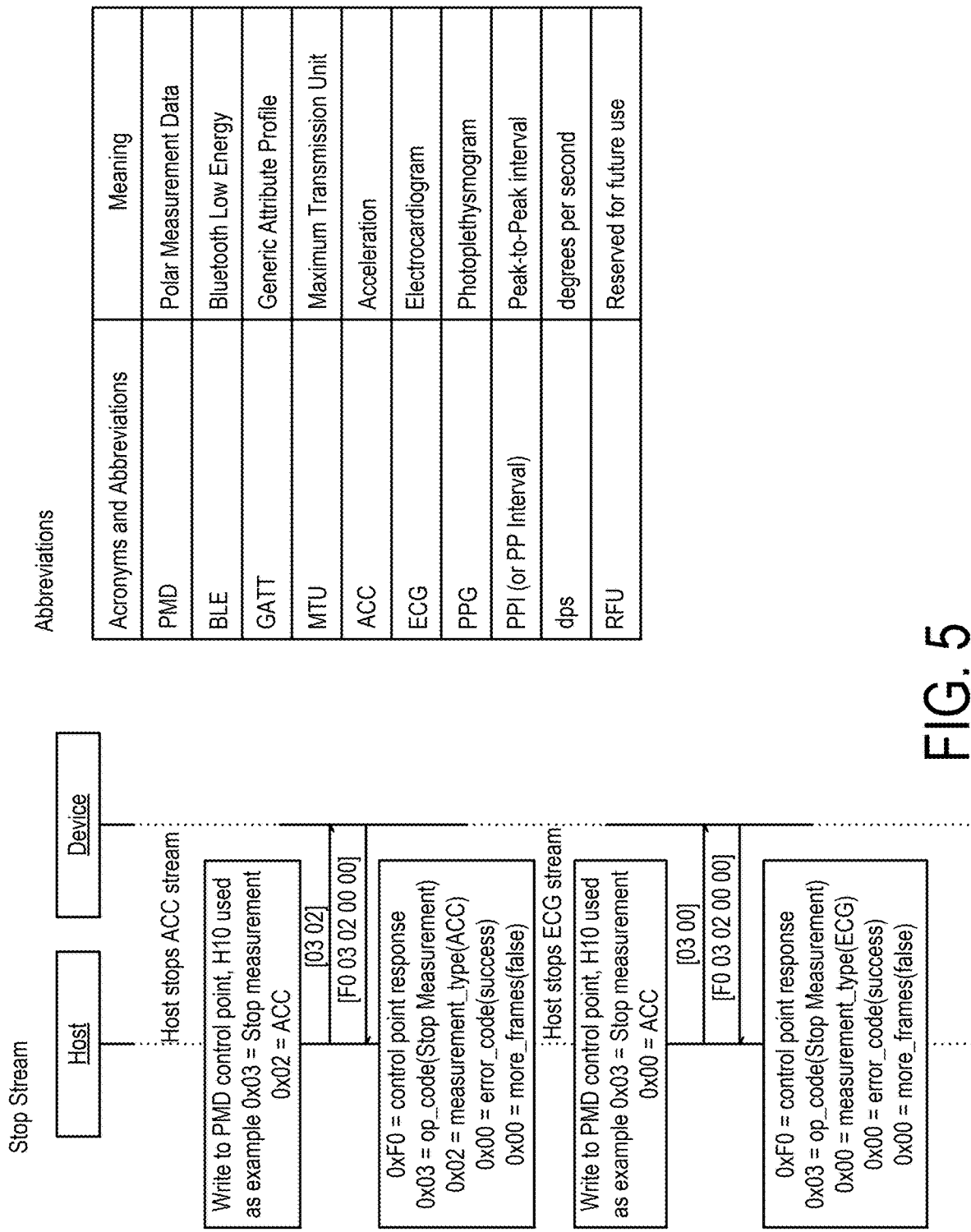
Figure 6:
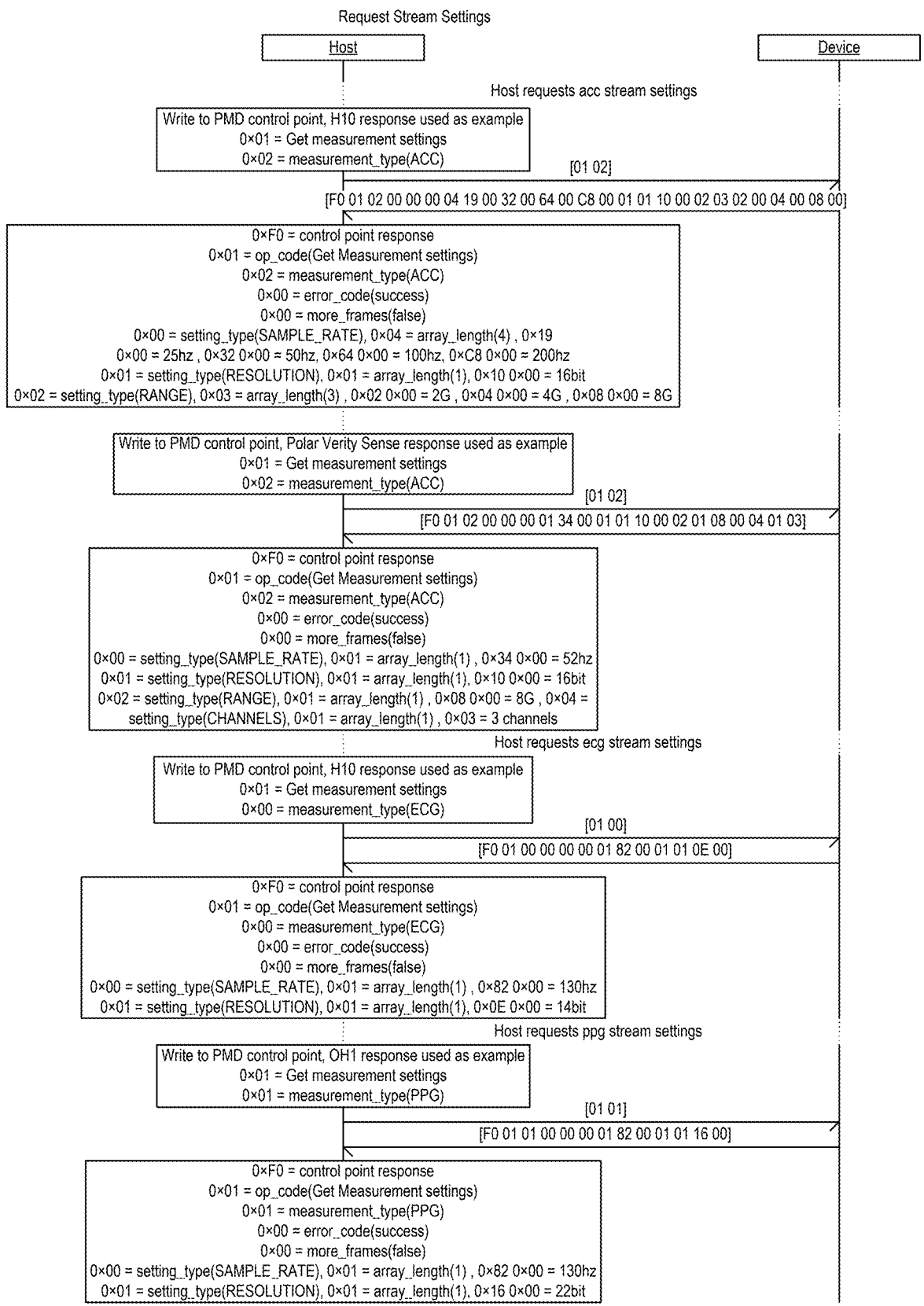
Figure 6:
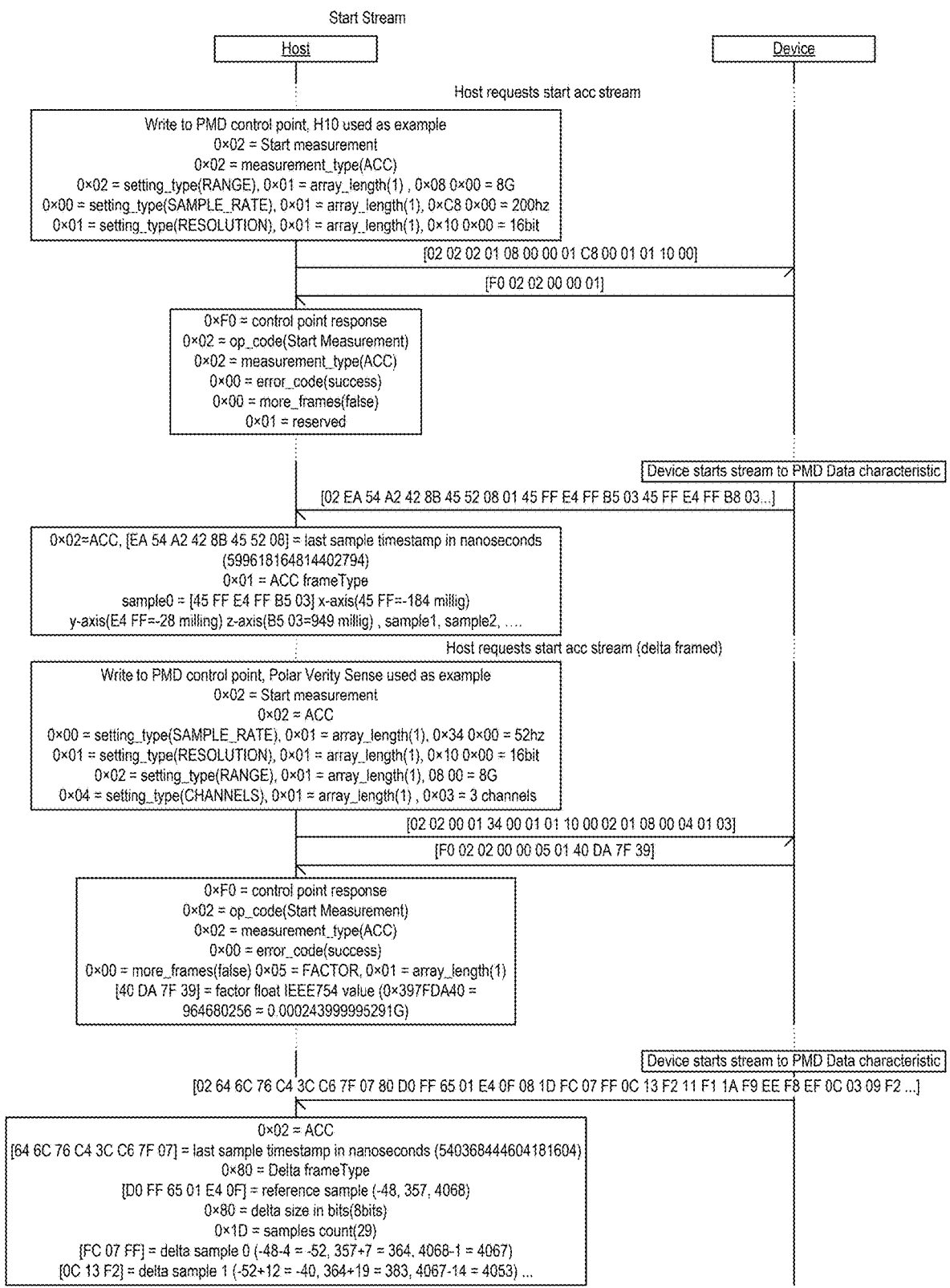

Next, FIGS. 4-6 show an example of GATT communication as applied to the Polar GritxX. The Bluetooth® Low Energy Technology defines two Generic Attribute Profile (GATT) roles:

a. A GATT Client that receives data sent via the Attribute Protocol and that sends Attribute Protocol requests, commands, and confirmations.

b. A The GATT Server that stores the data transported over the Attribute Protocol and that accepts Attribute Protocol requests, commands and confirmations from the GATT client. The GATT server also responds to requests and sends asynchronous indications and notifications to specified events.

The hub acts as a GATT server which is a device that sends information periodically and the GATT client is a mobile device that collects such information.

The Connected Device Protocol may support a GATT service relationship as shown and may define two distinct roles as follows:

a. Connected Device Client: The Client may use the Connected Device Service on the Connected Device Server. An example of a client device may be a mobile phone.

b. Connected Device Server: The Server may be an instantiation of the Connected Device Service. An example of a server device may be a watch or other mobile phone accessory.

The GATT API is utilized that defines the way in which two BLE devices transfer data using services and characteristics. GATT communications are considered to be exclusive, in that a BLE device can only be connected to a single device, such as a smartphone or tablet, at any given time. As soon as a BLE device connects to another device, that BLE device will stop advertising such that other devices will not be able to discover and connect with the BLE device until an existing connection to the single device (e.g., smartphone) is broken. GATT uses services to break data into logic entities and contain specific chunks of data or "characteristics." Each characteristic can encapsulate a single data point, which may correspond to an array of related data in some instances. Services and characteristics are all associated with individual identifiers, such as unique UUIDs, which can each be 16-bit for BLE services. Characteristics can also have values associated therewith that indicate permissions for the value, such as whether it can be read or written.

A GATT packet will have a maximum size, such as is specified by the Maximum Transmission Unit (MTU). The implementation of the Bluetooth stack can be a key factor in determining the GATT MTU on the various devices in at least some embodiments. The MTU in various Bluetooth-based embodiments is a value that is at least 23 bytes in length. Thus, when data is received to be transmitted, the data must be broken into chunks so it can be transmitted in packets that are, at most, of the MTU in size. It should be noted that some of the length of the packet corresponds to header information that is to be used for routing, as well as for reassembling the data from the packets received on the other device.

The system will upload data retrieved from the wearable devices to the CSP. In one embodiment the CSP automates data ingestion, alerting and data visualization for a range of seamless and fully automated integrations for hundreds of devices and apps. The system provides the following:

User Interface— A robust UI will be provided to monitor the data transmission/reception would be able to give a better insight into the system Backend—software to assimilate the data generated by the system with existing cloud APIs.

Hub acts as a conduit for the data passed by the devices such as watches, rings and straps to the cloud. If the bandwidth exceeds 40 simultaneous users, multiple BLE transceivers can be added to handle bandwidth Communication Protocol(s): The data can be passed further onto the cloud either using the standard protocols like HTTP(S), MQTT(S) etc. or even the cloud proprietary protocols like Google IoT, Azure Event Hub, Azure IoT Hub, etc.

FIGS. 7-10 shows a system that maximizes performance through the systematic application of sport science.

FIG. 7 shows a process that uses the hub syncing detailed above for athlete conditioning training. In this process:

Team leaders/coaches create plans that lay out a sequence of programs for all the relevant groups they want to train.

Members are assigned to one or more groups

Members register their mobile devices with the hub

Members enter a gym or a selected location containing the hub

Hub automatically collects personal data from the mobile exercise devices from various manufacturers and uploads to a cloud server Cloud server updates data for each user including KPI and KPV, health parameters, weight, height, among others.

Apply team training protocols to each member.

Team leaders/coaches review each member's progress on the plans and update the sequence of programs for all the relevant groups.

In one embodiment for military review, the system can provide fitness testing reports along with the wearable data syncs to enable a team leader to monitor skill acquisition, performance and testing results over time, and track progress against group and historical averages. The system can also collect and visualize psychological, aptitude, and general personality tests and cognitive tests. Injuries from training can be charted and visualized. The data can identify periods of optimal training and overtraining can be avoided. The quantity and type of injuries over a time period can be analyzed. Treatment ROI can be determined as the system enables users to see who's being treated, the most common treatments, and treatments by body area. With activity monitoring devices, the hub can discover trends and flag potential issues well ahead of time. Users can harness the power of data to make more informed decisions about capability & readiness, program effectiveness and strategy.

The team may have different groups with conditions. Team leaders can create plans that lay out a sequence of programs for all the relevant groups they want to train. As people are automatically added and removed from groups based on their training data, their training changes based on which groups they get assigned to. The team leaders or coaches can attach a program to their groups. Whenever a group's conditional logic is evaluated, people are added or removed according to the conditions. Whenever a person is added, they are assigned the attached program. Whenever a person is removed, the attached program is removed from their schedule. Within a program, the team leader/coach can add group tags to any of the workouts. When the program is assigned to a member, the member only receives tagged workouts if the member belongs to one or more of the groups tagged on the workout.

Figure 9:
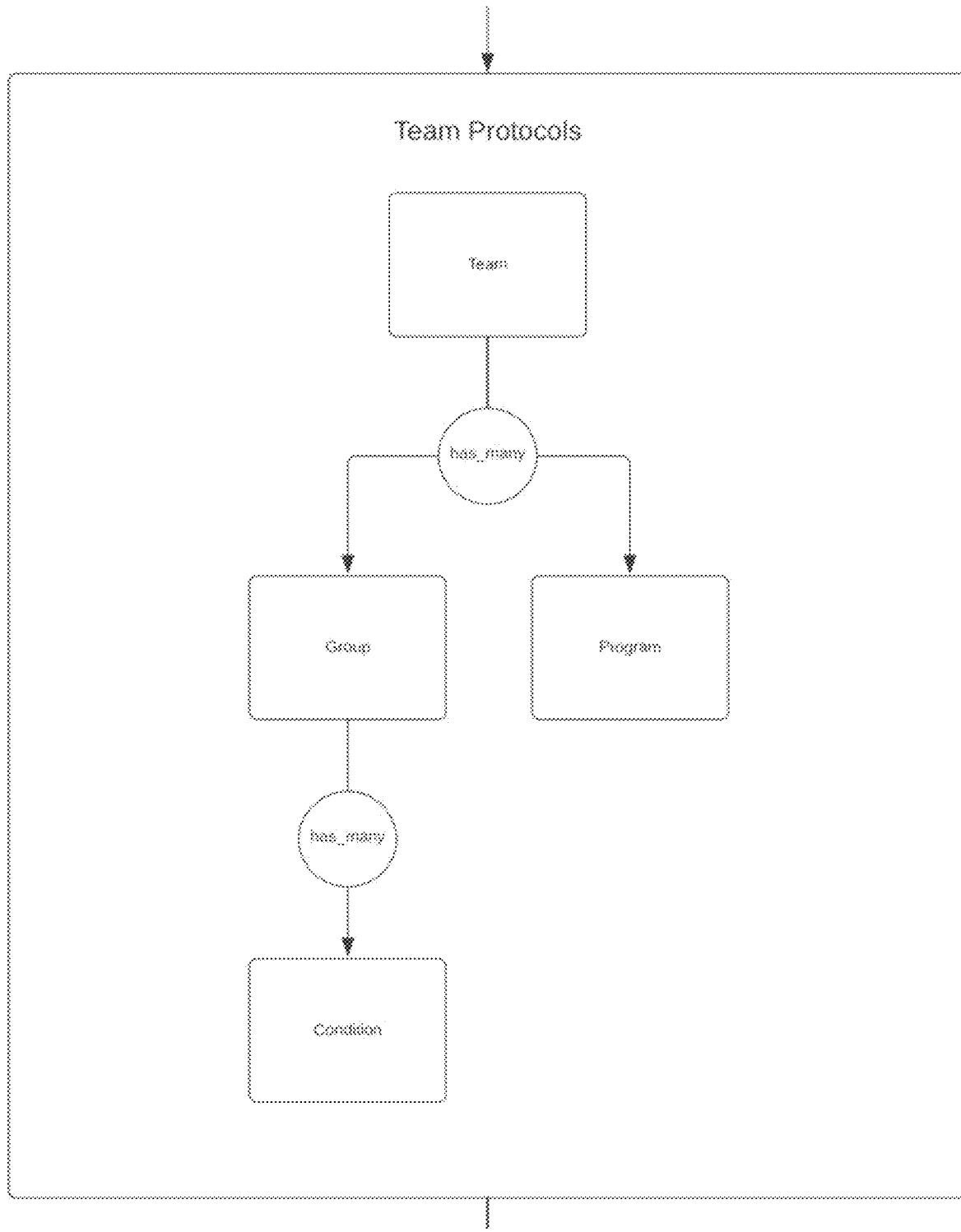
FIG. 9 shows exemplary team protocols.
Figure 10:
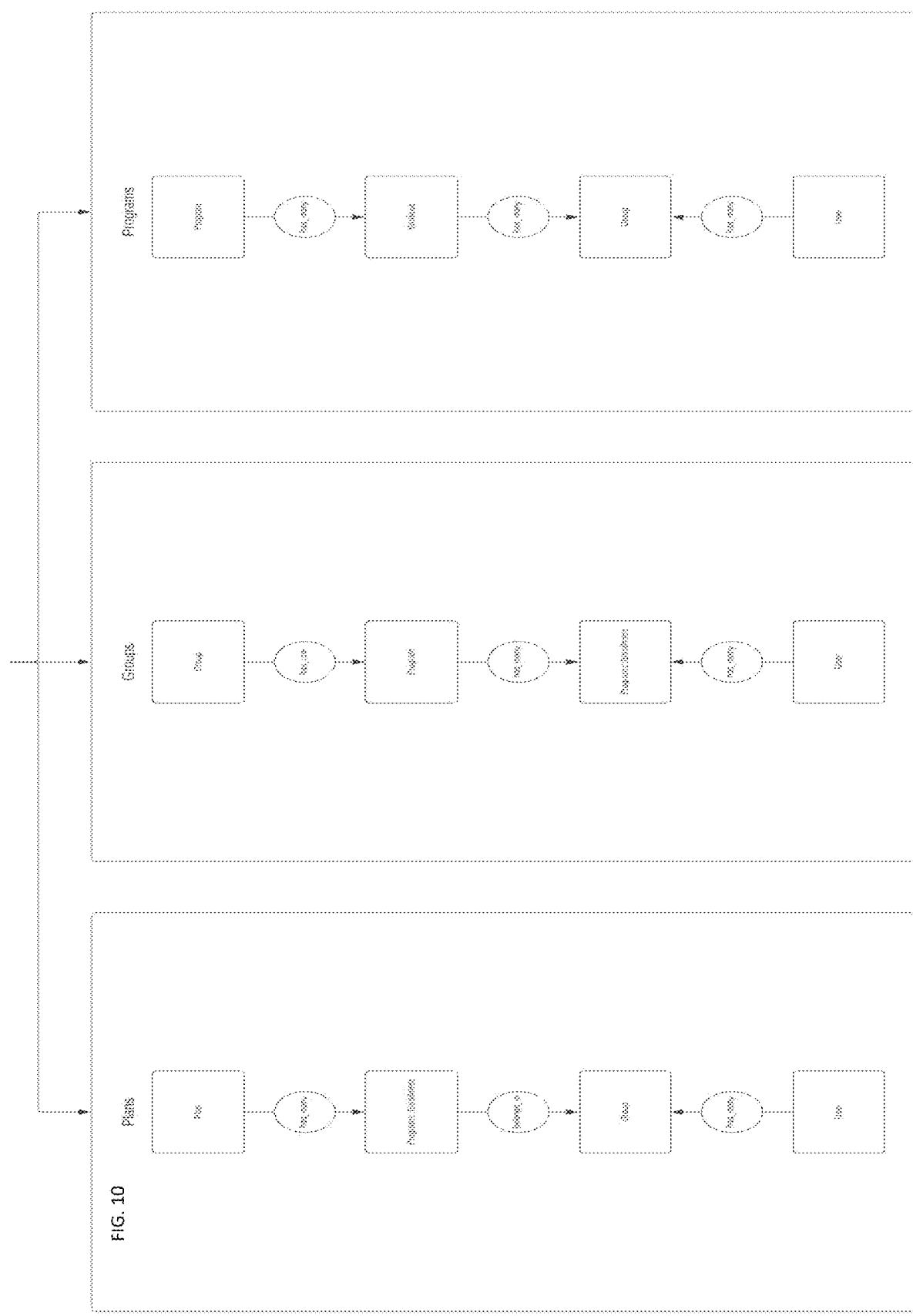
FIG. 10 shows exemplary processes for handling plans, groups and programs.

FIGS. 8-10 show exemplary conditioning training processes that can be carried out with or without the hub. FIG. 8 shows a user data diagram. Athlete data is stored for various metrics that coaches define and track. FIG. 9 shows team protocols. Coaches create protocols to determine how athletes should be trained. These protocols are defined within two constructs: programs and groups. Programs contain the training regimens for various objectives and adaptation goals. Groups are used to organize athletes into different training groups. Each group can have conditional logic that uses athlete data to determine which athletes should belong to the group. Athletes are automatically added and removed from groups whenever the relevant data is updated.

FIG. 10 shows processes for handling plans, groups and programs. Coaches can create plans that lay out a sequence of programs for all the relevant groups they want to train. As athletes are automatically added and removed from groups based on their athlete data, their training changes based on which groups they get assigned to. Coaches can attach a program to their groups. Whenever a group's conditional logic is evaluated, athletes are added or removed according to the conditions. Whenever an athlete is added, they are assigned the attached program. Whenever an athlete is removed, the attached program is removed from their schedule. Within a program, a coach can add group tags to any of the workouts. When the program is assigned to an athlete, they only receive tagged workouts if they belong to one or more of the groups tagged on the workout.

Test and monitor key performance indicators (KPIs) and key performance variables (KPVs). For example, the system can test and prescribe lifts based on 1RMs or on percentages of heart rate thresholds. All testing data is stored and accessible for tracking over time. The user can create groups of KPIs and KPVs to build assessments for important tests. For example, if users perform a counter movement jump test, the coach can group all the data points into a single assessment and build a custom formula to produce a calculated output from all the assessment inputs. This makes it easy capture data, manipulate the data, then use that data to inform training decisions. The system can configure sprint testing batteries with any intervals, then record the athlete's test results. Sprint profiles are captured for every athlete tested so coaches can optimize training and track progress over time. All calculations are done behind the scenes, so all the user has to do is copy and paste split times into the software. Automated decisions can be done. The system can add conditional logic to training groups that will automatically add or remove athletes from assigned programs based on the data collected. This includes any key performance indicators and key personal attributes that coaches collect directly from athletes. With the logic in place, athletes get dynamic interventions without looking at charts or making manual changes.

One embodiment uses a web-based spreadsheet to build training programs that feel natural and intuitive. Once a program is built, it can be deployed to as many athletes as needed. Users can quickly make modifications or create variants of the original program without having to modify the original. You can create programs that are either dynamic or periodized. They can also be programmed for any type of training, including strength training. To quickly analyze an athlete's training history and review the composition of a program, a training load visualizer is useful. This tool gives a snapshot of any training variable over time—reps, weight, distance, watts, calories, time, speed, heart rate—in terms of both volume and intensity to enable easy to use scientifically-backed training and conditioning programs. A coach can organize and plan training for athletes for any length of time (annual plans, quadrennial plans or one-month plans). The entire training cycle can be viewed in one view. Users can easily adjust the plan to suit their needs. To ensure athletes receive holistic, seamless care, the lead coach can include all coaches on the team.

A user can access the system to get a plan for their chosen sport, or to consult a coach to see plans for multiple athletes. FIG. 10 illustrates the entire process of the system after both the athlete and team data are entered into their respective databases. First, a coach creates a training program for a specific sport, either for an entire team or an individual athlete. The coach can initiate the request by user action, or it can happen automatically, for example, at a specific time of the year. The request is sent from the local terminal to the remote server via a computer network, such as the internet. The training plan builder and the training algorithm are stored on the remote server. The data is gathered from the team database and includes the athletes for whom the training plan is being built. The team data will typically include the sport or team the athlete is on as well as a list of dates that correspond to the year's schedule and any facilities data. The plan builder then uses the team data to choose a preconfigured training program from a training program database. If football is the selected sport, the program will be selected from the database. A training program is a collection of exercises that an athlete should perform. It also includes information about when and how they should be done. The training program doesn't include any information about the volume (sets/reps), or intensity of each exercise.

The next step is to extract specific exercise data from the exercise database 30, for each exercise in the chosen training program. These data will include the following: the name of each exercise; the description of each (including images or videos); any coaching points; the volume (sets/reps); and the numbers used to calculate the intensity. Next, data for each individual athlete is taken from the user database. This includes data about the athlete, including their performance in the initial strength tests, and any injuries.

The next step is to calculate the intensity (weight), for each exercise in the program using the exercise intensity algorithm. The intensity algorithm is only used to determine the recommended weights for each exercise, and it does not affect any training plan. Each exercise is given its own intensity. Once the plan is assembled, it can be viewed. Then the user will receive the training plan via the user interface. The user can view the plan directly at the interface or export it to another device or printer.

The system produces a customized training plan that can be tailored to each sport. It includes predetermined, static and unique exercises for each sport. The training plans are usually designed to help athletes train over a period such as a year. Each plan can be broken down into phases, seasons, weeks, or days. Each phase, season, week, day, or other period is designed to achieve specific goals. Together, they create an annual comprehensive training plan.

A training cycle is the whole year that an athlete spends training, from the start of the off-season through the end of the post season. The typical annual training cycle is made up of four to five training blocks, with four to five phases. A training phase is a series of short sessions that share a common exercise program but differ in intensity according to the exercise intensity algorithm. A training phase can last several weeks, one or more days.

Every training program for a specific sport is created in accordance to the movements that are associated with that sport's athletic performance. This does not mean that the exercises will be appropriate for all muscles and body parts. Every day's training program includes, among other things, a resistance-based warm up, an explosive or rapid motion, resistance training, injury prevention moves, speed/agility and resistance training. Each sport has a unique program that caters to each athlete and determines the time of each phase and week, according to the start and end dates of the season.

Next, strength and conditioning training is detailed. The athlete's personal information is saved in their profile. This profile can be modified in the system. The system maintains a profile of each athlete to allow for customizing performance training. An athlete who plays baseball as a catcher will receive a training program and sessions that focus on his movement needs. The system will determine the length of the training plan that is appropriate for each athlete. This plan can be four, eight, or twelve weeks in length. However, an athlete may be given a plan that is longer. The training plan is used to organize the sessions. The length and content of a training program can be modified for an athlete in different ways. This is dependent on factors like the athlete's sport and their physical condition.

The appropriate training sessions are chosen for each athlete. This is done to help them stay healthy and build momentum. The example system can take into consideration an athlete's playing time when assembling training sessions. In some embodiments, for example, if an athlete is in the offseason and the season starts at a specific time, the exercises are adjusted at appropriate training stages to ensure that the athlete is in peak condition and not exhausted from intense training.

Once the system has created a profile for an athlete and a training plan, the athlete can decide to train. Once the athlete is ready for training, he/she activates the user interface on his/her device to access exercises from the system. To determine an athlete's training history, the system uses his/her current profile. This includes whether the athlete took time off, how many days he/she has been training daily, and so forth. The system can adjust the exercises for the next training session based on the information in the athlete's profile. The system might request additional information from the athlete. In a pre-workout screen, an athlete might be asked for the most recent game status. An athlete might indicate that he/she has played a particular game in the days leading up to the training session. The athlete is also asked to describe the current level of soreness in different parts of his/her body and his/her energy level. An athlete might also be asked to identify where the training session will take place and what equipment is available at that location. According to the information provided by the athlete, the training session of the athlete may be modified. You should note that the information requested by the computer system and/or entered into it may differ from the information provided.

If the system has sufficient information to allow the system to generate and/or adjust a training session for the athlete, the training data may be displayed on the user's device, for example an overview of the entire training session. This overview could include information about the session's focus, equipment and exercises, as well as the cool-down and warm-up. An overview can also list the improvements that were made during the session. The weight of equipment used by an athlete may be recorded in the system to generate future training plans or training sessions. You can view the training session in either text mode or video mode. Text mode shows the training session exercises in seconds. The athlete must complete the exercises in the given time. An athlete can choose to display a video that shows how to do a particular exercise correctly and the benefits of doing the exercise. The coach will show the athletes how to perform the exercises in video mode.

After the athlete finishes the training session, he/she logs the effort in the system and gives feedback as required by the system. The system may adjust future sessions if the athlete indicates that one part of the training session is too difficult. An athlete might receive a training summary as well as a breakdown of the training session for that day. To display the benefits of the training session, the athlete can activate 36 screens on the device. The system can render videos that explain how an athlete exercises and how to choose the right equipment.

Next, for athlete tracking, one embodiment stores an athlete's training sessions and makes them available later by the athlete. Athletes can monitor their training on a daily, monthly or yearly basis. An athlete can monitor his/her training and investment in strength and conditioning over time and in detail. The system also stores the athlete's mental performance training. This allows the athlete to view, for example, all days in which they completed the morning or evening rituals mentioned above. An athlete can view a graph showing the daily grades he/she earned in relation to achieving daily targets. A user device can be used to connect with other users of this system. This includes friends, teammates, coaches, scouts and others. An athlete can view how their connections are creating their games, how often the athlete's friends accessed his/her profile, and many other things.

In some exemplary embodiments, a whole team can be trained. The team's coaches may then have access to the software platform, which allows them to see each member's strength, conditioning, mental performance training data, and progress. The team coach and athletes can share the same information in real-time about the status and progress of their athletes. Some embodiments allow a college coach to be a scout and use the system for recruiting. Coaches can view, in real-time, the strength, conditioning, and mental training of their team members, even if they are away for several months. A coach can see an athlete's training history and track it over time. The system also allows coaches to see trends in team performance.

In the weight room and on the field, all the tools needed to run training sessions can be found. A coach can display and record all activity of each athlete during a session using a digital whiteboard, or athletes can follow the coach's instructions and record their results. Users can also print PDFs that include personalized prescriptions. Coaches can communicate with their athletes, whether they are at the gym or away. The mobile app allows athletes to know what to do and coaches can see how their athletes are performing. The interface on the mobile app is easy to use and athletes can track their progress over time on key performance indicators.

A player development platform (PDP), in various examples, is designed to assist teams in improving their competitive performance. It organizes, manages, and tracks most, if not all, aspects of player development from one central location. These areas may include, but are not limited to, strength and conditioning, mental performance coaching, injury prevention, rehabilitation, and nutrition. A player development platform could be set up as a hub that is accessible to multiple users. This includes an athlete and coaching staff (e.g., head coach, assistant coaches).), medical staff (e.g. a team physician or an athletic trainer, a physical therapy therapist, etc.), a strength- and conditioning coach, as well as a nutritionist. In some embodiments, players who are involved with any of the player areas can communicate with other users. A coach may make recommendations regarding strength and conditioning for a player or team. This information can then be sent to other users, such as medical staff, who can provide comments and recommendations. A medical staff member can also observe an athlete and make comments about them. The hub can allow information about an athlete or team to be circulated around the platform and/or through it, so that all players who have been authorized by the player-development platform can receive the information and use it in organizing, managing, and/or tracking player growth. A team of users might use some of the player development areas, but not all.

Different types of players may use different player development software platform platforms in different roles. One user may have a specific role and thus use hardware or software that is different than hardware or software used by another user with a different role. An athlete is one example of such a role. In various embodiments, an athlete may have access to the best coaching and can also be customized for him. These coaching sessions can be accessed at any hour of the day or night by an athlete. The athlete can also monitor their mental and physical training and get assistance with injury rehabilitation and/or therapy. An athlete can use software applications, such as interactively on a smartphone, tablet and/or laptop, or on a desktop computer.

A coach, such as an assistant or head coach, may also be a user. An athlete's mental and physical training history may be monitored by a coach. A coach staff member can monitor an athlete's mental and physical training history and may also receive updates on any injury or inconsistency. A coaching staff member can use a software program, such as interactively on a smartphone, tablet, laptop, and/or desktop computer. A coach may be able to use the same software program as an athlete they are coaching.

A strength and conditioning coach may also be a user. They may distribute, manage, and/or create customized training programs for athletes on a mass-scale. This coach can also modify training plans quickly and easily on a large scale. They may also monitor an athlete's training history and/or receive real-time updates about soreness, injuries, or exercises that are too difficult. An athlete's medical team may also be a concern for a strength coach. A player development platform may include software that can be tailored to meet the specific needs and support the duties of a strength coach. A user dashboard that allows for customized training programs to be created, distributed, and managed by strength and condition coaches may be available in various embodiments. These programs can be distributed to athletes via the player development application. A strength coach can also access a library with specific programs and/or individual exercise options.

Dynamic training programs can be offered, for example, by a strength coach. These programs can dynamically adapt to the needs of an athlete, e.g. on a daily basis. An application engine can access a database using Firebase or another platform to determine if a training program was created for an athlete in various embodiments. If the answer is yes, an appropriate training session will be sent to the athlete. The engine can access cloud data storage to create a new training program. The session can be sent to an athlete if a new session is created for that particular athlete. For future use by other athletes, the new session can also be stored in the real time-accessible database. Although the real-time-accessible data base may be a SQL database, other databases platforms and options are possible.

A player development platform may allow medical staff to support athlete development. A team physician, an athlete trainer, and a physical therapist could all be part of the medical staff. They may be required to be notified about any athlete injuries. This is to help create, distribute, and manage rehabilitation and physical therapy strategies and to view an athlete's training history. A player development platform can provide software that is tailored to meet the needs and performance of such medical staff in various ways.

In different embodiments, nutritionists may play roles in supporting athletes' development through a player development platform. Software may be used, for example, to create and/or distribute customized meal plans or supplementation that align with an athlete's specific training strategy.

A library can provide a variety of educational videos on various topics, such as psychology, strategy, and state. A software application may allow an athlete to implement the knowledge he/she has acquired, such as "create your own game" or "generate a state" tools.

A player development platform may allow a team's medical staff to use the medical software. This software can be used to create, distribute, and/or manage custom rehabilitation and/or therapy programs. These programs may then be distributed to athletes via the software application. The database can be accessed by medical staff members who need to access specific training programs or individual exercises. Medical staff may have roles in supporting athlete development via a player development platform. Medical staff may include, e.g., a team physician, an athletic trainer, a physical therapist, etc. who may wish and/or need to be notified of any athlete injuries, to create, distribute and manage rehab and physical therapy strategies, and to see an athlete's physical training history. In various embodiments, a player development platform provides software specific to support the performance and needs of such medical staff.

A nutritionist might also use technology such as a nutrition software program on an electronic device. This could include a smartphone, tablet or desktop computer. The nutritionist might create and distribute personalized meal plans and supplementation to match the player's training program.

A training program database stores preconfigured training programs. It contains all preconfigured training programs that are part of the overall system. The exercise database can be included in the training program database. A training program is a set of exercises that are specifically designed to meet a training purpose. Each program is saved in the database as a single program. It cannot be modified by inputs from the user or the team. Each program loaded with training programs is specific to a sport. It includes a preselected set of exercises that the athlete can perform. One training program is preferred for each sport. The present embodiment does not allow the user to alter the content of a training program. However, other embodiments might allow users to modify the structure of a specific training program by changing the number or intensity of exercises.

The system supports Individualized Fitness—No One Size Fits All. The system treats every athlete as unique and each person's response to training can be different depending on their genetics, gender, age, sex, and many other factors. The system applies an evidence-based approach that considers individual variability and applies the science of exercise adaptation to each situation. Science will help you know where to begin, but it is often necessary to experiment to find the best for each individual athlete. To find out if cardio induces people to eat more than usual to make up for lost energy from exercise, a group of researchers did a meta-analysis and concluded that individuals don't compensate for the energy they expend during exercise. The other study showed that there was a lot of variation in the amount of food people eat after a cardio session. Below is a chart that was adapted from the study. It shows how individuals differ in their compensatory eating habits. Another study examined the inter-individual variability of muscle responses to resistance training.

Because everyone is different, the best exercise program for every athlete is one that's tailored to them. Personalized program design is influenced by the athlete's experience in a particular sport, movement, and task. "Experience" does not necessarily refer to skill or ability in the context of athletic training. It refers to an athlete's adaptive capacity and their position along the athletic performance curve. Advanced athletes are more adaptable than beginners, which means that they can move faster. Advanced athletes, however, are already approaching their genetic limits and have made progress. A personalized training program must be tailored to the individual athlete to instill adaptation at a reasonable pace. You will likely experience suboptimal performance and risk of injury, overtraining and regression if you train below or above your adaptive capacity.

In another embodiment, the system adjusts for age. The maximum heart rate and cardiac output drop, which decreases oxygen delivery to the muscle. The Type II muscle mass is particularly affected by this decrease. An older body loses its resilience and takes longer to recover. This has consequences for the appropriate volume, intensity, and recovery time. These changes do not disqualify older athletes for training hard, but they must also train smart. Fitness prescriptions must reflect the body's needs and capabilities. Older athletes can avoid injuries and maximize performance by following an age-conscious exercise program.

In another embodiment, the system accounts for gender. Women are more different from men (obviously). Many differences can be attributed to early childhood and cultural conditioning. However, genetic and physiological differences are very real between the sexes. Women shouldn't train like men because of differences such as: Women are more likely to eat a high-fat diet; Higher reps are better for women; Women can handle more volume; Women should be less aggressive in their training; Stable state cardio is more appealing to women than HIIT for their health; Women perform better when the lifting speed is slower; Women are more tolerant to metabolic stress than men; Women need less rest between sets than men; and Women can train at a higher frequency than men. While men and women have similar physiological and genetic characteristics, it is important to not over-generalize. Women (and men) will undoubtedly have different traits and/or more ambiguous answers than the "norm."

In another embodiment, genetics data is used to influence training. The body's ability lose fat, build muscle, and increase endurance is strongly influenced by genetics. The interaction of genes (nature) with environmental factors (nurture), is complex. We don't know enough about the effects of certain genes on chemical processes and their expression in response to environmental conditions. For example, take the ACTN3 gene. This gene instructs the body to make a protein called Alpha (a)-Actinin-3. It is mostly found in Type II muscles fibers. Elite sprinter status requires the 577RR genotype. One study found that only 1 in 12 international-level runners had working copies of this gene. ACTN3 is a key component of strength, speed, and endurance. However, it's not a guarantee that a particular variant of a gene will be present. For example, the ACE genotype may be responsible for better endurance training with high intensity and low volume, while the D-allele might be associated with better strength development through higher intensity and lower volume resistance training.

All activities should be tracked and measured, not just key performance indicators. This will allow you to determine cause and effect between what athletes do and the results. You can then experiment with different variables to determine how athletes react to stress levels and recovery times.

The system thus provides a strength- and conditioning management platform that lets users create individualized programs at large scale and track every athlete's performance and analysis. The number of factors that influence individual variation is likely too many to incorporate into a training program. Some of these variables, such as the effects of family, work, and sleep quality, collected by the wearables through the hub can be used to adjust and personalize the training. With the system, users can experiment, measure the results, and adjust the variables until we find a solution that works best. The system enables training where no two athletes are alike. Every person is unique, so everyone is not treated with the same prescriptions and the same routines to everyone in a team.

The instant people management systems with individualized charts and dashboards allows users/coaches to see a group of charts or data points when faced with a decision and make an informed choice. Such decisions can be made on a monthly or even weekly basis. For example, each month a user might evaluate indicators of strength and endurance, then use that info to determine the upcoming month's training focus. However, if the user needs to make data-driven decisions on a day-to-day basis, looking at several charts each day becomes rather inefficient. The user can't evaluate readiness scores for a team of 20+ athletes, then make adjustments to their individual routines day in and day out.

Figure 11:
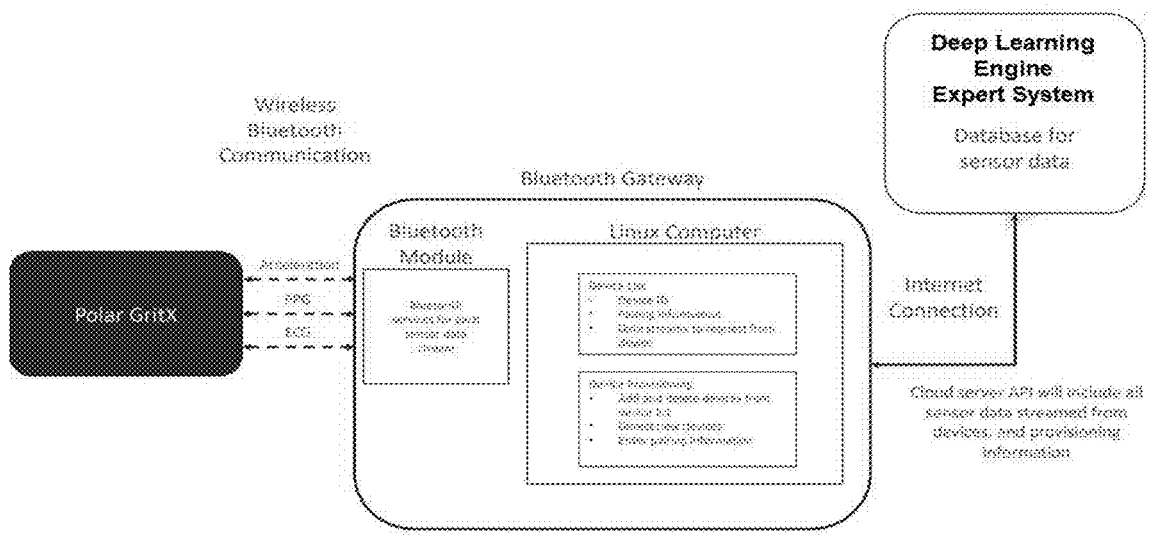
FIG. 11 shows an exemplary learning machine or expert system processing data from the hub.

To address this issue, the system provides two tools: AI and decision trees. The AI/expert system or decision tree modules can run on a remote server as shown in FIG. 11, but the machine learning system can also be distributed and run on the hub itself.

Decision trees are a great tool for bridging the gap between collecting data and taking action. Building a decision tree with IF THEN conditions force the coach to clearly define the logic that should be applied based on the data collected (if this, then that). Clearly documenting the decision criteria helps you consistently apply the same logic to achieve your desired outcomes. It also enables users to evaluate the quality of decisions and make refinements as users continue to learn more objectively.

If the coach has already selected the athletes to train and the area of training she wants to implement, she'll start the decision tree by laying out the possible interventions. As an example, let's consider a simple strength training scenario. The coach has a base program that athletes follow, but circumstances may exist on any given day when their routine should be modified. In one example, there may be four possible variations of the exercise program: 1) Full-go, where the athlete is cleared to do the program as originally prescribed; 2) Half-volume, where the athlete should do a less intense variation of the day's workout; 3) Recharge, where the athlete should be assigned a low-volume workout to allow for more recovery; and 4) Check-in, where the athlete should consult with a coach before doing any work that day.

The inputs are then refined. Typically, only a few metrics impact the result, and the marginal benefit of evaluating additional data quickly diminishes. In this example five measurements that are most important to our decision: stress, sleep, fatigue, mood, and soreness. Data from the wearable device for these measurements are collected from the athletes daily from the Bluetooth hub, and we'll assign them to one of the four interventions listed above depending on their responses.

Figure 12A:
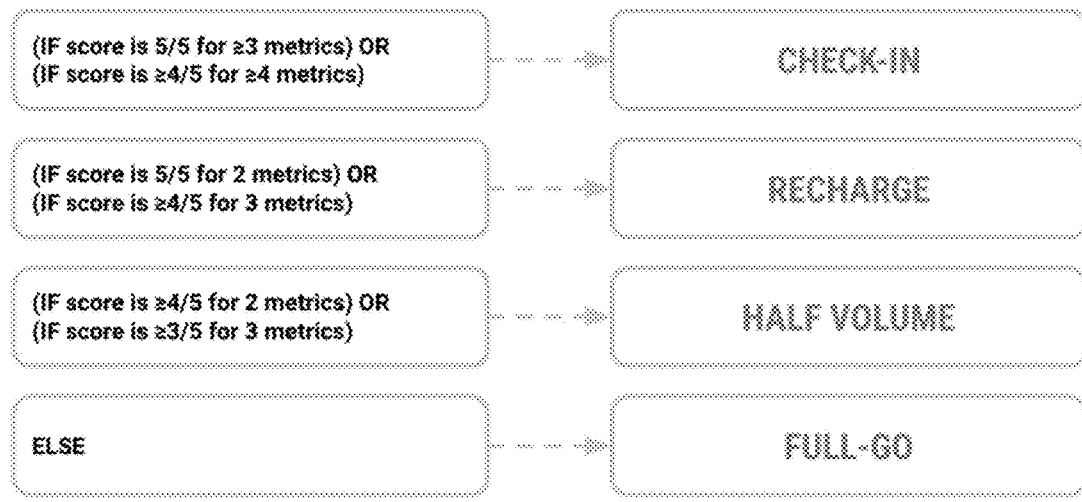
FIG. 12A shows an exemplary expert system (If Then Rules)

Continuing with the example, if an athlete scores a 5/5 on 3 or more of the metrics OR they score a 4/5 or higher on 4 or more of the metrics, the athlete needs to check-in with a coach: (IF score is 5/5 for ≥3 metrics) OR (IF score is ≥4/5 for ≥4 metrics)=>Check-in. Using the same notation for all four branches, a decision tree such as FIG. 12A is generated. The system allows you to build decision logic, collect data, then make automated, real-time adjustments to training interventions. Once the user sets up the IF THEN logic, he/she never needs to look at the data. Athletes get the appropriate interventions without anyone analyzing numbers or looking at a chart. The idea is to create a workflow where building programs, collecting data, and executing data-driven decisions are all part of a seamless process, and to automate as much of it as possible. This will amplify user impact as a coach and allow the user to unlock the power of sport science for the athletes.

The automated data collection capability of the present system supports a cadence for the frequency of data capture and evaluation with the decision tree or AI logic. With the present tools, coaches and team leaders can embed testing and data collection right into the training process with minimal interruption to the training program or the coach's workflow.

Once the decision tree logic is defined, the data collection process is solid at an appropriate cadence, the data capture capability allows coaches to see if the decisions actually get carried out. The logic trees deliver the right training to the right athlete at the right time.

In an alternative embodiment, deep learning is used to extract important variables and relationships to automatically adjust the training routine on behalf of the coach. The details of the deep learning engines are shown in FIG. 12 and described in depth below.

In addition to improving training, the AI/deep learning system can be used to recommend team members based on a project requirement. As decision makers such as team leaders (in military/commercial settings) or strength & conditioning professionals (in sports settings) are often overburdened as it is. They are responsible for the health and performance of many athletes at once, so it's a battle to find time for improving processes and becoming more efficient. It usually happens incrementally over a long time. The system can create automated logic and workflow where collecting data, making decisions, and prescribing training interventions, all part of a seamless, automated process.

In a military embodiment, the system provides a method of improving a skill set of an soldier, comprising the steps of determining a skill profile of each of a set of soldiers; determining a set of characteristics of required for a project, the characteristics and the skill profile having correlated features; selecting an available soldier having a skill profile anticipated to be sufficient to handle the project, said skill profile being indicative of a lower level of skill with respect to at least one of the set of characteristics than another available soldier; and adding the selected available soldier to the team and employing the project as a training exercise. Advantageously, the selected soldier may not be penalized based on performance during the training exercise. The skill profile may be updated after the training exercise to represent a higher level of skill with respect to the characteristics of the project, and/or based on a utility of the project. The selecting may be based on an optimization of the utility and cost of the communication, the soldier training resulting from the training exercise being a component of the utility. The soldier selection may also be optimized based on a cost-utility function, said cost-utility function comprising a valuation of immediate costs and utilities and a valuation of persistent soldier training costs and utilities.

In one embodiment, the system provides a method of improving a skill set of an agent, comprising the steps of determining a skill profile of each of a set of agents; determining a set of characteristics of required for a project, the characteristics and the skill profile having correlated features; selecting an available agent having a skill profile anticipated to be sufficient to handle the project, said skill profile being indicative of a lower level of skill with respect to at least one of the set of characteristics than another available agent; and adding the selected available agent to the team and employing the project as a training exercise. Advantageously, the selected agent may not be penalized based on performance during the training exercise. The skill profile may be updated after the training exercise to represent a higher level of skill with respect to the characteristics of the project, and/or based on a utility of the project. The selecting may be based on an optimization of the utility and cost of the communication, the agent training resulting from the training exercise being a component of the utility. The agent selection may also be optimized based on a cost-utility function, said cost-utility function comprising a valuation of immediate costs and utilities and a valuation of persistent agent training costs and utilities.

In a sports embodiment, the system provides a method of improving a skill set of an athlete, comprising the steps of determining a skill profile of each of a set of athletes; determining a set of characteristics of required for a project, the characteristics and the skill profile having correlated features; selecting an available athlete having a skill profile anticipated to be sufficient to handle the project, said skill profile being indicative of a lower level of skill with respect to at least one of the set of characteristics than another available athlete; and adding the selected available athlete to the team and employing the project as a training exercise. Advantageously, the selected athlete may not be penalized based on performance during the training exercise. The skill profile may be updated after the training exercise to represent a higher level of skill with respect to the characteristics of the project, and/or based on a utility of the project. The selecting may be based on an optimization of the utility and cost of the communication, the athlete training resulting from the training exercise being a component of the utility. The athlete selection may also be optimized based on a cost-utility function, said cost-utility function comprising a valuation of immediate costs and utilities and a valuation of persistent athlete training costs and utilities.

In another embodiment, a system to provide a method of allocating a resource to handle a task, comprising the steps of: determining a task-handling load; identifying a characteristic of a task to be handled; in dependence on said determined task-handling load, selecting a handling protocol selected from the group consisting of: selecting a first trainable resource predicted to have deficient skills relating to the task based on the identified characteristic, while also selecting a second resource capable of assisting in training the first trainable resource with respect to the characteristic; and selecting a third resource predicted to have sufficient skills relating to the task based on the identified characteristic, wherein according to a selected protocol, a trainable resource is trained with respect to the at least one characteristic, or a sufficiently skilled resource handles the task. Preferably, the third resource has skills which are optimum for handling the task. Typically, a plurality of tasks are simultaneously handled, and a selected third resource has optimum skills with respect to the available resources and the identified characteristics of the tasks to be handled. Preferably, the system is provided for training humans, i.e., the trainable resource comprises a human. For example, the environment may be a military project, where the soldiers are trained to have skills predicted to be required by incoming or outgoing project requirements. The selecting step comprises, for example, retrieving a resource profile, comprising a set of metrics corresponding to the set of identified characteristics. The protocol selection may be based on a threshold task-handling load for a group of resources. The skill or imputer skill of a resource may be updated after selection thereof and/or successful completion of an assigned task, and/or based on a performance during task handling.

According to another embodiment, each resource has skills which are classified as a multidimensional vector, and wherein the identified task to be handled has a characteristic represented as a predicted multidimensional vector of required skills of a handling resource, wherein a selected first resource and second resource together have a composite multidimensional skill vector which substantially corresponds to the predicted multidimensional vector of required skills.

According to another embodiment, the second resource has a training skill for remediating a skill deficiency with respect to the identified characteristic, such that after handling the task, the first resource skills are improved.

Another embodiment provides a plurality of available trainable first resources, wherein a particular first resource is selected based on which trainable first resource is predicted to have a maximum value gain in skills as a result of selection. Likewise, a plurality of second resources may be available, wherein a particular second resource is selected based on which second resource is predicted to be able to impart a maximum value gain in skills as a result of selection. Further, a plurality of first and second resources may be available, wherein a particular set of first and second resources are selected based on which set of first and second resources is predicted to have an optimum gain in skills for the first resource and lowest overall cost, as a result of the selection of the set.

In another embodiment, a group of resources having sufficient skills for handling the task are aggregated, with a first resource having a worst skill set for handling the task selected from the group.

Another embodiment is optimized long-term cost utility. For example, resources are selected based on an optimum long-term cost utility of such selection, including training costs, and anticipated future improvements in resource skills based on training opportunities.

Another embodiment provides a method wherein the identification step comprises anticipating issues to be raised in handling the task, the selecting step comprising analyzing profile records of resources with respect to the anticipated issues to determine a minimum capability requirement, training requirement of a first resource, and a training capability of a second resource with respect to the anticipated issues, selecting a first resource having a skill exceeding the minimum capability requirement to handle the anticipated issues and having a training requirement with respect to the anticipated issues, and selecting a second resource having a training capability with respect to the anticipated issues, whereby a selected first and second resource have sufficient skills to handle the anticipated task, while the second resource assists the first resource in improving task handling capabilities.

Yet another embodiment provides a method for determining an efficient schedule for a plurality of agents in a fulfilment center, balancing fulfilment center efficiency and agent training opportunity, each of the plurality of agents having a skill profile, comprising the steps of predicting an aggregate set of characteristics for delivery workload during a contiguous period of time; selecting a set of agents having a target aggregate distribution of skills, including training agents having a skill set deficient with respect to the set of characteristics and trainer agents having a skill set permitting them to train the training agents with respect to the characteristics; scheduling the training agents and trainer agents for the contiguous period of time; and pairing training and trainer agents corresponding for the work.

As will be explained more fully below, the team member selection is determined based on a long-term optimization algorithm, which balances project needs, individual skills, system preferences, and/or prior training. FIG. 13 shows an exemplary process for matching team members to a task or project. Extending from FIG. 7's training process, the team deployment process is as follows:

Team leaders/coaches create plans that lay out a sequence of programs for all the relevant groups they want to train.
Members are assigned to one or more groups
Members register their mobile devices with the hub
Members enter a gym or a selected location containing the hub
Hub automatically collects personal data from the mobile exercise devices from various manufacturers and uploads to a cloud server
Cloud server updates data for each user including KPI and KPV, health parameters, weight, height, among others.
Apply team training protocols to each member.
During Training: Team leaders/coaches review each member's progress on the plans and update the sequence of programs for all the relevant groups.
Pre-Deployment Team Match: Team leaders/coaches identify common requirements (for example speed, strength, expertise in language/skill, . . . ) to AI system (deep learning/expert system or simulated annealing) and provide exercise/program data, training data, and prior mission data to AI system for training and to create one or more AI models/expert system rules
During Deployment: Team leaders/coaches provide current mission's requirements to deep learning/expert system for recommendation. AI system applies AI models/expert system rules to current data and checks the latest temporal data from wearable/mobile fitness data and makes recommendations. Compressed/reduced version of the AI models is provided to field team leaders or tactical commanders for local operation or adaptation or in case access to cloud is unavailable.

The team recommendation framework which considers both individual and team level characteristics for team recommendation. A first deep learning machine is applied to learn the weight of each feature from prior project outcomes. A team strength score is generated using the weighted features, and a second deep learning machine is applied to find the approximate optimal team. Then an expert system or ruled based (if then) engine is applied to make the final recommendations. The rules-based assignment engine may perform a thorough, programmatic comparison between project needs and requirements and personnel factors including qualifications, skills, workload, strength, speed, equipment familiarity, social relationship with other team members, availability, and other factors. In one example, the system selects team members after performing the following operations in addition to processes of FIGS. 7 and 13:

Receive Project Requirements
Predict Project Skill Requirements
Look at Similar Projects and Identify candidate Members matching Skill Requirements
Retrieve Member Performance from the Hub
Apply training and skill-based factors to prune Prospective Members using simulated annealing or other methods
Optimize Cost-Utility Function for Project based on:
  Expected incremental utility of member
  Expected incremental cost of trainer
  Expected incremental training utility
Assign Members to Team (with coach available if a training session)

For example, in the sports world, fitness goals such as speed, strength, sport skills may be all that is needed for a game (mission). Speed is a game changer! In baseball speed causes pitchers and catchers not to focus on pitch execution. Infielders are forced to shift in and out of their positions to protect a potential steal. The game is accelerated by fast base-runners, which can cause the defense to rush. In addition to speed, strength from muscle bound sluggers, advanced metrics can be tracked for station-to-station baseball and other Statcast metrics such as Sweet Spot % (SwSp %), Barrels, Exit Velocity (EV), Batted Ball Distance (DST), Projected Home Run Distance (HR-DST), Launch Angle (LA) and Batted Ball Events (BBE). Coaches can focus on exercise parameters that improve the metrics. Team leaders/coaches can specify parameters to be tracked and machine learning/expert systems can be applied to correlate these parameters to "wins" or success objective(s). The machine learning can be used to iteratively make changes to the exercise sets specified. The system can be used in a way similar to the Oakland Athletics' Moneyball approach where the team is selected based on their skill sets, and at a much higher granularity of details based on in depth data provided with the wearables/hub sync.

Additionally, many tasks in business and in the military require people are multifunctional experts in core functions. They possess specific skill sets to support operations using conventional and nonstandard logistics. Fitness (strength and speed) as well as critical thinking skills and the ability to communicate effectively are paramount. These logisticians must be able to influence outside, within, and between disparate organizations and chains of command. They must possess technical skills and the ability to apply those skills in austere environments, often acting alone. They must be broadly experienced and adaptable across all levels of war (tactical, operational, and strategic). Understanding industrial base capability and capacity is critical. They must be able to operate in the joint, interagency, intergovernmental, multinational, and commercial framework. In a military example, the project requirement can be culled from the mission statement answering: Who will execute the operation (unit/organization)? What is the unit's essential task (tactical mission task)? When will the operation begin (time/event) or what is the duration? Where will the operation occur (AO, objective, and grid coordinates)? And Why will the force conduct the operation (for what purpose or reason)?

The skill sets required for team success can be determined by the team leader or coach, and training data captured by the hub can be used to create models that are then deployed to select members of the team optimal for success. Further, data such as injury or sleep condition the day before the mission can be used to update the team member selection process.

Simulated Annealing can be used with the AI/expert system, and it is a method for solving bound-constrained as well as unconstrained optimization parameter models regarding mission objectives that are set by the coach/team leader as shown in FIG. 12C.

One exemplary method uses physical annealing to reduce system energy. A random point is generated in every simulation of annealing. The distance between the current and new points is used as a basis for the probability distribution based on the temperature scale. The algorithm seeks to minimize the objective by incorporating certain probabilities and constraints. Accepted points that raise the goal are accepted because they allow us to look at all possible solutions, rather than focusing on the local minima. Simulated annealing optimizes by decreasing the temperature and minimizing search area of the personnel skill sets. Simulated annealing with AI can be performed using a series of steps. These steps include:

Simulated Annealing randomly creates a trial-point. A probability distribution determines the distance between the current and trial points. This distribution scale is temperature. Point distribution distance can be set by using the annealing function test. The trial point is gradually moved to keep the boundaries in place.
Simulated Annealing determines whether the new point is superior to the older. The new point that is better is accepted as the next point. If it is not, the acceptance function for simulated annealing allows it to be accepted.
The temperature is gradually reduced using a systematic algorithm that selects the most efficient point.
The annealing parameters, which raise and reduce the temperatures, are used to lower the values. Based on the possible gradients for each dimension of the objective, the simulated annealing parameter are calculated.
Simulated annealing ends when it reaches the lowest minima or meets any other specific stopping criteria.

Simulated annealing continues until the value is less than the tolerance function and the process stops when the algorithm reaches the maximum iteration value. When the maximum number is reached, the annealing ends. The default value for maximum time is selected where the algorithm will stop.

AI is optionally used to select the optimum simulated annealing model with other data. In embodiments, the assignment engine may access documentation or records to identify necessary qualifications or factors which may guide the assignment specific people to the project. According to embodiments of the invention in a further regard, a coach or team manager may manipulate a management application or interface to accept, or override given personnel assignments, to evaluate alternate providers, to view resulting matches to project requirements, to adjust various schedules and view other simulations or projected results or schedules. According to embodiments of the invention in a further regard, the management interface may flag potential conflicts between a provider's background and a project's needs. For example, a supervisor may be alerted that the reassignment of a person to a project may be contraindicated by skill, certification, strength, scheduling, or other factors. In some cases, the engine can recommend a person who is suboptimal with a profile which indicates that the person is likely capable of handling the work but requires training with respect to calls having the set of identified characteristics.

Figure 12B:
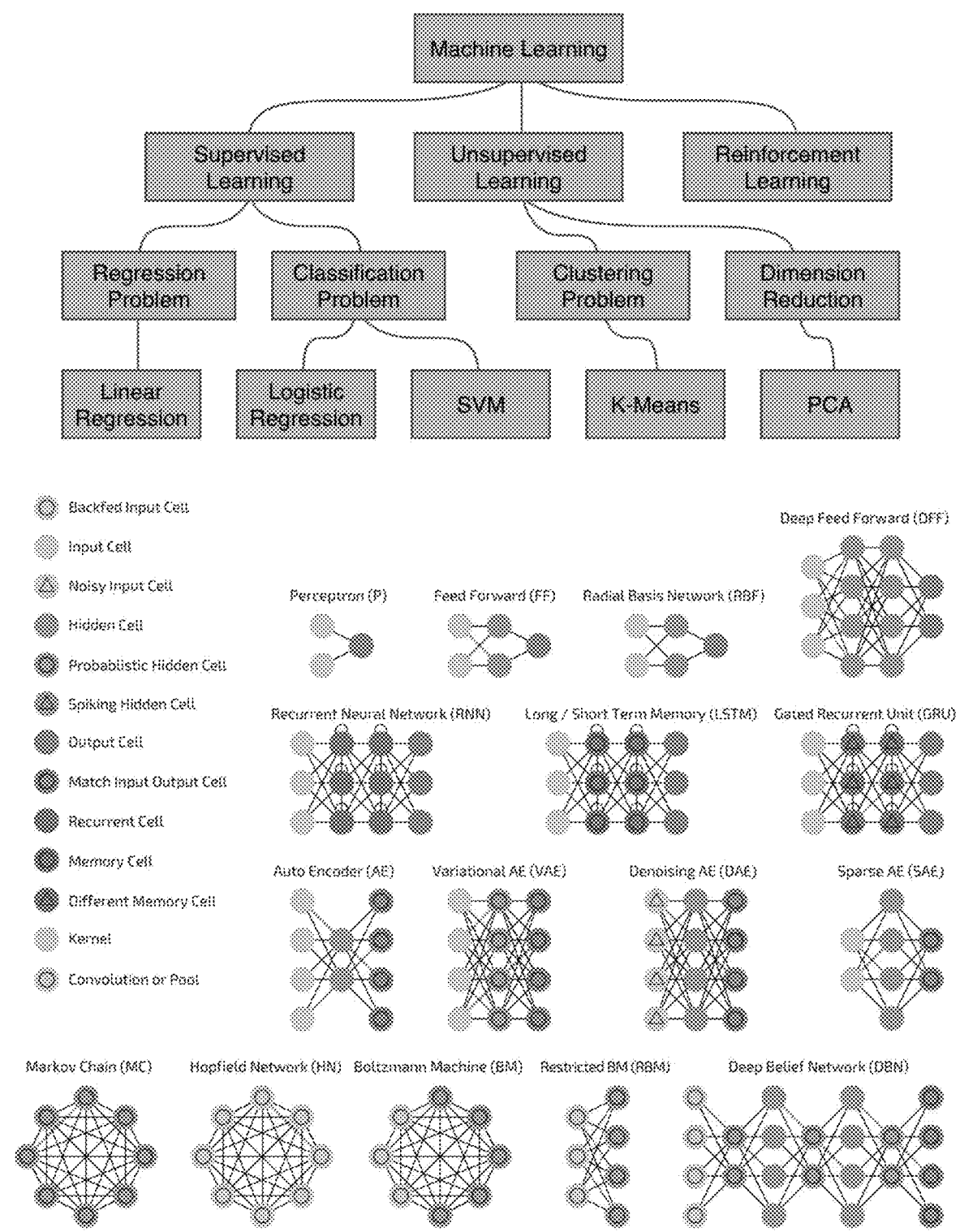
FIG. 12B shows exemplary deep learning systems.

FIG. 12B shows exemplary learning machine architectures applied to the data collected by the hub. The athlete/personnel dataset is explored on (Shallow) Neural Network and Deep Neural Networks. A simple NN can be considered as an extended version of Logistic Regression that is used to classify classes in a dataset. In a Shallow Neural Network, an input layer contains all the features of all training examples. In the hidden layer, training data are multiplied with weights and an activation function is applied. Generally, at the hidden layer, tanh, ReLU, leaky ReLU, Randomized ReLU, or other activation functions are used. At the output layer, sigmoid is used in binary classification problems and softmax is used in multiclass classification problems. Different cost functions such as MSE or RMSE can be used. However, these types of cost functions when used in classification problems result in a nonconvex function of all loss functions and will have multiple local minima. Therefore, cross-entropy loss function is used as the resultant sum of all cost functions is in a convex shape and therefore does not have the problem of local minima.

In another embodiment, original full neural network can be trained in the cloud, and distillation is used for teaching smaller networks using a larger "teacher" network. Combined with transfer learning, this method can reduce model size without losing much accuracy. This machine learning system can also be distributed and run on the hub itself. In one embodiment, the learning machine is supported by a GPU on a microprocessor, or to reconfigure the FPGA used as part of the baseband processing as neural network hardware.

While deep learning/neural networks have been detailed, the following alternatives are contemplated. Linear Discriminant analysis is generalized form of Fisher Linear Discriminant. It is dimension reduction technique which is used to model dissimilarities between two or more classes. Naive Bayes classifiers are probabilistic classifiers which are based on Bayes theorem assumes that all features are independent. Decision tree constructs the classification models in the pattern of tree structure. It divides the data into smaller and smaller subgroup where the final result is a leaf node, and outcome is represented by branch. SVM (supervised machine learning) algorithm performs classification by finding hyperplane between the classes. XGBoost is associated with the family of boosting algorithms as it uses a gradient boosting algorithm at its core. Boosting algorithms aggregates weak classifiers into the strong classifier. XGBoost is the ensemble method of decision tree classifier. It provides faster tree prunning. KNN is non-parametric classification method. It classifies new points based on the distance measures (Euclidean, Manhattan, etc). It gives prediction in less amount of time and easy to interpret those outputs.

In one embodiment, ultra-high-resolution video feeds and camera-carrying drones in a stadium or gym track how individual players' joints flex during a game, how high they jump or fast they run—and, using AI, precisely identify athletes' risk of injury in real time. Combining the system with the coaching programs detailed above can provide highly customized prescriptions for exercises and drills to help reduce injury risk. Computer-vision technology like the ones used at airport checkpoints for facial recognition will make this analysis possible. The app can compare the videos of users to a database that contains professional pitchers' moves. This allows it to recommend prescriptive drills to improve throwing efficiency. Machine learning algorithms, which crunch statistical data from sensors to analyze body movement and position changes that can indicate fatigue, weakness or injury are now more widely used. This information can be used to create training plans and to determine the best time to rest. Sensors can be worn by athletes, and AI methods identify the takeoff-and-landing of an act such as a jump and can also estimate that the stresses on the body that are quite high. In predicting injury risk, algorithms access the hub to gather long-term data for athletes who move from one team to the next every few years. Sensors may have different data, and visual data can be collected remotely without worrying about a sensor failing. Performance can't be easily measured because of psychological and emotional factors. These include stress during contract negotiations, fights with spouses, or bad food the night prior. The only way to test the algorithms is to see if a player flagged as a potential risk by the AI program actually gets hurt during a game. The system uses anonymized data to avoid data privacy issues, as well as the question of compensation for athletes if data is collected by teams to feed AI algorithm. The training data as well as AI processed broadcast TV video from teams all over the world tracks the speed and location of individual players can be used to reduce injury as well as screen potential candidates as the next player for recruiting purposes.

Energy Management/Air Quality uses are detailed next. In implementations, the hub reduces energy usage through a building management system (BMS) based on a number of mobile devices communicating with the hub and locations of the mobile devices. For example, if the hub detects activities only in a portion of a building, the hub instructs a building management system to minimize energy usage for lighting/heating in unused sectors of the building.

In yet other implementations, the hub protects occupants by managing in-door air quality. The hub identifies team members with a pandemic symptom or an endemic symptom by looking up temperature and heart rate of occupants and if the pattern fits Covid pattern, for example, the system then increases air flow or air quality in a building according to a number of mobile devices in a sector (indoor positions) of the building that are communicating with the hub. The hub can also restrict entry to the sector and enforces the minimum separation between occupants (such as the 6 ft separation rule for Covid, for example) by texting the mobile devices and advising occupants of the risks.

While the above describes commercial or multi-tenant building uses, the hub can be used for home settings to protect elderly as well. As shown in FIG. 14, this is done by having the hub to be the master synchronizer for numerous consumer monitoring devices that communicate over a PAN such as Bluetooth or Zigbee, among others. In one embodiment, the system can operate in a home, a nursing home, or a hospital. In this system, one or more mesh network appliances are provided to enable wireless communication in the home monitoring system. Appliances in the mesh network can include home security monitoring devices, door alarm, window alarm, home temperature control devices, fire alarm devices, among others. Appliances in the mesh network are all synced with the hub and can be one of multiple portable physiological transducer, such as a blood pressure monitor, heart rate monitor, weight scale, thermometer, spirometer, single or multiple lead electrocardiograph (ECG), a pulse oxymeter, a body fat monitor, a cholesterol monitor, a signal from a medicine cabinet, a signal from a drug container, a signal from a commonly used appliance such as a refrigerator/stove/oven/washer, or a signal from an exercise machine, such as a heart rate. For example, within a house, a user may have mesh network appliances that detect window and door contacts, smoke detectors and motion sensors, video cameras, key chain control, temperature monitors, CO and other gas detectors, vibration sensors, and others. A user may have flood sensors and other detectors on a boat. An individual, such as an ill or elderly grandparent, may have access to a panic transmitter or other alarm transmitter. Other sensors and/or detectors may also be included. The user may register these appliances on a central security network by entering the identification code for each registered appliance/device and/or system. The mesh network can be Bluetooth network, Zigbee network or 802.15 network.

The system can detect light, sound and people present to provide an accurate determination of occupancy and such determination can be used to effectively provide environmental comforts for the occupants. One exemplary process for room environmental control is shown in FIG. 15 as follows:

```
Check occupancy sensing via mobile device activities collected by the hub, and
    if no one is in a room, turn off one or more appliances such as lighting
    and display terminals in the room and turn off heat or AC (ventilation
    system);
    else
        Turn on light and ventilation system;
        Adjust air management system for the number of occupants detected
        Check for symptoms of Covid (temperature/heart rate/breathing rate)
            If symptoms detected then
                Warn occupants of risk;
                Enforce minimum distancing requirements
                Increase air flow in the room and vent air in room to outside (no
                recirculation)
```

A user override button is provided so that the user can manually force the room to turn on appliances as desired.

A mesh network appliance can be connected to a power line to communicate data to and from the mesh network. A smart meter can relay data to a utility over the power line and the mesh network to the appliance. The smart meter includes bi-directional communication, power measurement and management capability, software-controllable disconnect switch, and communication over low voltage power line. A remote processor that can remotely turn power on or off to a customer, read usage information from a meter, detect a service outage, detect the unauthorized use of electricity, change the maximum amount of electricity that a customer can demand at any time; and remotely change the meters billing plan from credit to prepay as well as from flat rate to multi-tariff. The appliance minimizes operating cost by shifting energy use to an off-peak period in response to utility pricing that varies energy cost by time of day. A rechargeable energy reservoir such as a fuel cell or a battery can supply energy to the appliance, and the reservoir is charged during a utility off-peak period and used during a utility peak pricing period. Solar panels, windmill, or other sources of renewable energy can be provided outside the premises to generate local energy that recharges the reservoir or store energy in the utility grid.

The appliance's operation is customized to everyone's preference since the system can identify each individual through his or her heart rate signature, among others. Each user can set his or her preferences and the system can detect the user's entry into a room and automatically customizes the room to the user. For example, upon entry into a room, the network can stream the user's preferred music into a music player in the room or alternatively can stream his or her favorite TV shows and display on a screen for the user. Also, lighting level and temperature can be customized to the user's preferences. The bed setting can be customized to reflect the user's preference for a soft or hard mattress setting. The chair height, tilt/reclination and firmness can be adjusted to the user's preference. The window transparency or tint can be automatically set to the user's preferred room brightness. Phone calls can automatically be routed to the user's current position. If there are many people in the room, the appliance's operation is customized to a plurality of individuals in a room by clustering all preferences and determining a best fit preference from all preferences.

Since the system can track user position quite accurately, the system can store and analyze personal information including medicine taking habits, eating and drinking habits, sleeping habits, or excise habits. The information can be used to track the user's general health.

For users that are at risk of stroke, the positional data, heart rate, and breathing rate/respiration rate, as well as change delta for each, can be data mined to determine the user's daily activity patterns. A Hidden Markov Model (HMM) recognizer, a dynamic time warp (DTW) recognizer, a neural network, a fuzzy logic engine, or a Bayesian network can be applied to the actual or the difference/change for a particular signal, for example the heart rate or breathing rate, to determine the likelihood of a stroke attack in one embodiment.

In another embodiment, a Doppler radar positioned near the heart can pick up the heartbeat corresponding to as the S1-S4 heart sounds and determine the likelihood of a stroke from the heart movements that generate the sound patterns for S1-S4. The progression of heart failure (HF) is typically accompanied by changes in heart sounds over time. First, an S4 heart sound may develop while the heart is still relatively healthy. Second, the S4 heart sound becomes more pronounced. Third, as deterioration of the left ventricle continues, S3 heart sounds become more pronounced. Sometimes, this is accompanied by a decrease in S1 heart sounds due to a decrease in the heart's ability to contract. Thus, ongoing or continuous monitoring of heart sounds would greatly assist caregivers in monitoring heart disease. However, individual patients may exhibit unique heart sounds that complicate a generalized approach to heart sound monitoring. For example, the mere presence of an S4 heart sound is not necessarily indicative of heart disease because normal patients may have an S4 heart sound. Another complication develops if a patient experiences atrial fibrillation when an ischemia occurs. In this case a strong atrial contraction, and the associated S4 heart sound, is likely to be absent due to the atrial fibrillation. This results in an increase in the S3 heart sound without an associated S4 heart sound or without an increase in an S4 heart sound. Therefore, the progression of heart disease, such as HF and an ischemic event, is typically better monitored by establishing a patient-specific control baseline heart sound measurement and then monitoring for changes from that baseline. The baseline could be established in one or several different criteria, such as at physiologic or pathophysiologic state, at a specific posture, at a particular time of day, etc.

The mesh network comprises code to store and analyze personal information including heart rate, respiration rate, medicine taking habits, eating, and drinking habits, sleeping habits, or excise habits, among others.

In one embodiment for home monitoring, the user's habits and movements can be determined by the system for fall or stroke detection. This is done by tracking location, ambulatory travel vectors and time in a database. If the user typically sleeps between 10 pm to 6 am, the location would reflect that the user's location maps to the bedroom between 10 pm and 6 am. In one exemplary system, the system builds a schedule of the user's activity as follows:

| Location | Time Start | Time End | Heart Rate |
|---|---|---|---|
| Bed room | 10 pm | 6 am | 60-80 |
| Gym room | 6 am | 7 am | 90-120 |
| Bath room | 7 am | 7:30 am | 85-120 |
| Dining room | 7:30 am | 8:45 am | 80-90 |
| Home Office | 8:45 am | 11:30 am | 85-100 |
| ... | | | |
| ... | | | |

The habit tracking is adaptive in that it gradually adjusts to the user's new habits. If there are sudden changes, the system flags these sudden changes for follow up. For instance, if the user spends three hours in the bathroom, the system prompts the third party (such as a call center) to follow up with the patient to make sure he or she does not need help.

In one embodiment, data driven analyzers may be used to track the patient's habits. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient's habits or ambulation patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, several different analyzers or models are built by presenting different parts of the training data as test sets to the analyzers in an iterative process. The parameter or model structure is then determined based on the combined performance of all models or analyzers. Under the cross-validation approach, the analyzer or model is typically retrained with data using the determined optimal model structure.

In general, multiple dimensions of a user's daily activities such as start and stop times of interactions of different interactions are encoded as distinct dimensions in a database. A predictive model, including time series models such as those employing autoregression analysis and other standard time series methods, dynamic Bayesian networks and Continuous Time Bayesian Networks, or temporal Bayesian-network representation and reasoning methodology, is built, and then the model, in conjunction with a specific query makes target inferences.

Bayesian networks provide not only a graphical, easily interpretable alternative language for expressing background knowledge, but they also provide an inference mechanism; that is, the probability of arbitrary events can be calculated from the model. Intuitively, given a Bayesian network, the task of mining interesting, unexpected patterns can be rephrased as discovering item sets in the data which are much more—or much less—frequent than the background knowledge suggests. These cases are provided to a learning and inference subsystem, which constructs a Bayesian network that is tailored for a target prediction. The Bayesian network is used to build a cumulative distribution over events of interest.

In another embodiment, a genetic algorithm (GA) search technique can be used to find approximate solutions to identifying the user's habits. Genetic algorithms are a particular class of evolutionary algorithms that use techniques inspired by evolutionary biology such as inheritance, mutation, natural selection, and recombination (or crossover). Genetic algorithms are typically implemented as a computer simulation in which a population of abstract representations (called chromosomes) of candidate solutions (called individuals) to an optimization problem evolves toward better solutions. Traditionally, solutions are represented in binary as strings of 0s and 1s, but different encodings are also possible. The evolution starts from a population of completely random individuals and happens in generations. In each generation, the fitness of the whole population is evaluated, multiple individuals are stochastically selected from the current population (based on their fitness), modified (mutated or recombined) to form a new population, which becomes current in the next iteration of the algorithm.

The system allows patients to conduct a low-cost, comprehensive, real-time monitoring of their parameters such as ambulation and falls. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office. The user may give permission to others as needed to read or edit their personal data or receive alerts. The user or clinician could have a list of people that they want to monitor, and have it show on their "My Account" page, which serves as a local central monitoring station in one embodiment. Each person may be assigned different access rights which may be more or less than the access rights that the patient has. For example, a doctor or clinician could be allowed to edit data for example to annotate it, while the patient would have read-only privileges for certain pages. An authorized person could set the reminders and alerts parameters with limited access to others.

The server may communicate with a business process outsourcing (BPO) company or a call center to provide central monitoring in an environment where a small number of monitoring agents can cost effectively monitor multiple people 24 hours a day. A call center agent, a clinician or a nursing home manager may monitor a group or several users via a summary "dashboard" of their readings data, with ability to drill-down into details for the collected data. A clinician administrator may monitor the data for and otherwise administer several users of the system. A summary "dashboard" of readings from all Patients assigned to the Administrator is displayed upon log in to the Portal by the Administrator. Readings may be color coded to visually distinguish normal vs. readings that have generated an alert, along with description of the alert generated. The Administrator may drill down into the details for each Patient to further examine the readings data, view charts etc. in a manner similar to the Patient's own use of the system. The Administrator may also view a summary of all the appliances registered to all assigned Patients, including but not limited to all appliance identification information. The Administrator has access only to information about patients that have been assigned to the Administrator by a Super Administrator. This allows for segmenting the entire population of monitored Patients amongst multiple Administrators. The Super Administrator may assign, remove and/or reassign Patients amongst several Administrators.

When a call from a patient arrives at a call center, whether the call has been pre-processed at an SCP, the telephone number of the calling line and the medical record are made available to the receiving switch at the call center by the network provider. This service is available by most networks as caller-ID information in one of several formats such as Automatic Number Identification (ANI). Typically, the number called is also available through a service such as Dialed Number Identification Service (DNIS). If the call center is computer-enhanced (CTI), the phone number of the calling party may be used as a key to access additional medical and/or historical information from a customer information system (CIS) database at a server on the network that connects the agent workstations. In this manner information pertinent to a call may be provided to an agent, often as a screen pop on the agent's PC/VDU.

The call center enables any of a first plurality of physician or health care practitioner terminals to be in audio communication over the network with any of a second plurality of patient wearable appliances. The call center will route the call to a physician or other health care practitioner at a physician or health care practitioner terminal and information related to the patient (such as an electronic medical record) will be received at the physician or health care practitioner terminal via the network. The information may be forwarded via a computer or database in the practicing physician's office or by a computer or database associated with the practicing physician, a health care management system or other health care facility or an insurance provider. The physician or health care practitioner is then permitted to assess the patient, to treat the patient accordingly, and to forward updated information related to the patient (such as examination, treatment and prescription details related to the patient's visit to the patient terminal) to the practicing physician via the network.

It is noted that, while preferred embodiments of the invention involve the training of human agents, the invention is not so limited. The agents, which may be considered resources, may be automated devices which are capable or learning or training, e.g., so-called artificial agents, or even animals or other biological or hybrid systems. The state of the resource is preferably measured, predicted or modeled, to provide a skill set, skill profile, or aptitude rating. In some instances, e.g., where there is sufficient capacity in the system to permit short-term inefficiencies, a training mode or protocol is instituted, wherein the trainable resources are presented with training challenges. In this way, the resources are improved. On the other hand, when the available capacity is limited or deemed insufficient, a high-efficiency mode or protocol is adopted, to fill a short-term demand on the system. Generally, a resource selected for efficient operation will differ from a resource for training operation, though this is not necessarily the case: an agent capable of training to perform a task generally has minimally sufficient skills for handling the task, albeit at lower efficiency than a trained resource. Likewise, even in the case of automated systems, it is sometimes undesirable to simply "clone" or copy a resource; rather, the internal logic and efficiency of such resources may differ; the trainer resource, for example, may have limited skills, be computationally inefficient, slow, require additional resources, or have high cost. (The trainer resource for an artificial agent may be, for example, a human.)

If it is said that an element "A" is coupled to or with element "B," element A may be directly coupled to element B or be indirectly coupled through, for example, element C. When the specification or claims state that a component, feature, structure, process, or characteristic A "causes" a component, feature, structure, process, or characteristic B, it means that "A" is at least a partial cause of "B" but that there may also be at least one other component, feature, structure, process, or characteristic that assists in causing "B." If the specification indicates that a component, feature, structure, process, or characteristic "may", "might", or "could" be included, that particular component, feature, structure, process, or characteristic is not required to be included. If the specification or claim refers to "a" or "an" element, this does not mean there is only one of the described elements.

An embodiment is an implementation or example. Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. It should be appreciated that in the foregoing description of exemplary embodiments, various features are sometimes grouped together in a single embodiment, figure, or description thereof for the purpose of streamlining the disclosure and aiding in the understanding of one or more of the various novel aspects. This method of disclosure, however, is not to be interpreted as reflecting an intention that the claimed embodiments requires more features than are expressly recited in each claim. Rather, as the following claims reflect, novel aspects lie in less than all features of a single foregoing disclosed embodiment. Thus, the claims are hereby expressly incorporated into this description, with each claim standing on its own as a separate embodiment.

Many of the methods are described in their most basic form, but processes can be added to or deleted from any of the methods and information can be added or subtracted from any of the above description without departing from the basic scope of the present embodiments. It will be apparent to those skilled in the art that many further modifications and adaptations can be made. The particular embodiments are not provided to limit the concept but to illustrate it. The scope of the embodiments is not to be determined by the specific examples provided above but only by the claims below.

What is claimed is:

1. A method to process data, comprising:
pairing selected wearable devices with a hub, wherein the selected wearable devices have at least two different profiles syncing to at least two different databases that do not share fitness or health data or interoperate with each other;
determining capabilities of a wireless connection through a set of defined services that each comprise a set of supported characteristics and communicating with each mobile device using the determined capabilities;
automatically copying data in each mobile device when the mobile device within a range of the hub;
uploading the copied data to a remote server;
parsing the data based on each device manufacturer data; and
synchronizing the parsed data with a cloud or remote database to provide a single point access to fitness or health data from the selected wearable devices.

2. The method of claim 1, comprising managing energy usage in a building according to number of mobile devices communicating with the hub.

3. The method of claim 1, comprising performing forced synchronization of known wearables without user action and without a smartphone.

4. The method of claim 1, comprising identifying by the hub one or more assigned wearable devices, pulling data from devices, and pushing data to a cloud storage provider (CSP).

5. The method of claim 1, comprising saving sync data with a date and time.

6. The method of claim 1, comprising reading a Generic ATTribute Profile (GATT) database to determine capabilities of a Bluetooth connection.

7. The method of claim 1, wherein the devices that do not share data with each other include one or more of: watch, ring, chest band, medical device, home security device, camera, phone, speaker, television, refrigerator, washer, dryer, car, garage door, pill bottle, cooking appliance, thermostat, fire alarm, door lock, light bulb, water meter, electric meter.

8. The method of claim 1, comprising providing the synchronized data to an athlete data management or analytics platform to prevent injuries and improve athlete performance.

9. The method of claim 1, comprising providing the synchronized data to a personnel data management or analytics platform to prevent injuries and improve personnel performance.

10. The method of claim 1, comprising generating one or more strength and conditioning workouts and tracking injury, prescribing rehabilitation, and managing return-to-play right along side the one or more strength and conditioning workouts.

11. The method of claim 1, comprising applying a machine to select a team to solve a task or to update a training protocol.

12. The method of claim 1, comprising applying hub data to revise a training protocol based on predetermined events or to identify potential members of a team with one of: Perceptron, feed forward network, radial basis network, recurrent neural network, long/short term memory, gated recurrent unit, auto encoder (AE), variational AE, denoising AE, sparse AE, Markov chain, Hopfield network, Boltzmann machine (BM), restriction BM, deep belief network.

13. The method of claim 1, comprising training with hub data to revise a training protocol based on predetermined events or to identify potential members of a team using one of: supervised learning, unsupervised learning, reinforcement learning.

14. The method of claim 1, comprising applying simulated annealing, deep learning, or if-then rules to hub data to revise a training protocol based on predetermined events or to identify potential members of a team.

15. A method, comprising:
pairing selected mobile devices with a hub, wherein the selected mobile devices have at least two different profiles syncing to different databases that do not share data or interoperate with each other;
determining capabilities of a Bluetooth connection through a set of defined services that each comprise a set of supported characteristics and communicating with each mobile device;
automatically copying data in each mobile device when the mobile device within a range of the hub;
uploading the copied data to a remote server;
parsing the data based on each device manufacturer data;
synchronizing the parsed data with a cloud or remote database to provide a single point access to data from all selected mobile devices;
managing access, air flow or air quality in a building according to number of mobile devices communicating with the hub.

16. A method to process data, comprising:
pairing selected wearable devices with a hub, wherein the selected wearable devices have at least two different profiles syncing to at least two different databases that do not share fitness or health data or interoperate with each other;
automatically copying data in each mobile device when the mobile device within a range of the hub;
uploading the copied data to a remote server;
parsing the data based on each device manufacturer data; and
synchronizing the parsed data with a cloud or remote database to provide a single point access to fitness or health data from the selected wearable devices;
training members based on one or more training protocols;
automatically collecting mobile device data and reviewing a member progress and updating the training of members of the one or more groups;
and
retrieving wearable or mobile data and generating one or more personnel training recommendations.

17. A system, comprising:
a hub syncing data from selected personal area network (PAN) fitness or health monitoring devices having at least two different profiles syncing to different databases that do not share data or interoperate together; and
code running on the hub to:
pair the plurality of mobile devices with the hub;
determine capabilities of a PAN connection through a set of defined services that each comprise a set of supported characteristics and communicating with each mobile device;
collect mobile device data from group members;

automatically copy data with member characteristics in the mobile device and extract data from the mobile devices when each of the group members are within a range of the hub;

upload the copied data to a remote server that parses the data based on each manufacturer data and synchronizes data from all selected PAN devices with a cloud or remote database; and provide a single point of access for data from all selected PAN devices with the cloud or remote database.

18. The system of claim 17, wherein the hub reduces energy usage through a building management system (BMS) based on a number of mobile devices communicating with the hub and locations of the mobile devices.

19. The system of claim 17, comprising code to collect data from a plurality of devices in a home and applying deep learning to predict living patterns of a person and to call for assistance if one of the devices detect a health problem or if the living patterns deviate from norm.

20. A system, comprising:

a hub syncing data from selected personal area network (PAN) fitness or health monitoring devices having at least two different profiles syncing to different databases that do not share data or interoperate together; and code running on the hub to:

pair the plurality of mobile devices with the hub;

determine capabilities of the mobile devices where each comprise a set of supported characteristics and communicating with each mobile device;

collect mobile device data from group members;

automatically copy data with member characteristics in the mobile device and extract data from the mobile devices when each of the group members are within a range of the hub;

upload the copied data to a remote server that parses the data based on each manufacturer data and synchronizes data from all selected PAN devices with a cloud or remote database;

provide a single point of access for data from all selected PAN devices with the cloud or remote database, wherein the hub manages air flow or air quality in a building according to a number of mobile devices communicating with the hub and locations of the mobile devices.

* * * * *